United States Patent
Zhu et al.

(10) Patent No.: US 6,346,534 B1
(45) Date of Patent: Feb. 12, 2002

(54) GONADOTROPIN-RELEASING HORMONE RECEPTOR ANTAGONISTS AND METHODS RELATING THERETO

(75) Inventors: Yun-Fei Zhu; Keith M. Wilcoxen, both of San Diego; R. Scott Struthers, Encinitas; Chen Chen, San Diego; Patrick J. Connors, Jr., San Diego; Yinghong Gao, San Diego; Fabio C. Tucci, San Diego, all of CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 0 days.

(21) Appl. No.: 09/570,239

(22) Filed: May 12, 2000

Related U.S. Application Data

(60) Provisional application No. 60/219,316, filed on Sep. 23, 1998, provisional application No. 60/193,335, filed on Jul. 28, 1999, and provisional application No. 60/287,591, filed on May 11, 1999.

(51) Int. Cl.[7] ....................... A01N 43/54; A61K 31/505; C07D 487/00; C07D 239/70
(52) U.S. Cl. .......................... 514/258; 544/281; 544/282
(58) Field of Search .......................... 514/258; 544/281, 544/282

(56) References Cited

U.S. PATENT DOCUMENTS

| | | | |
|---|---|---|---|
| 5,140,029 A | 8/1992 | Kennis et al. | 514/272 |
| 5,744,479 A | 4/1998 | Furuya et al. | 514/301 |
| 5,780,437 A | 7/1998 | Goulet et al. | 514/19 |
| 5,849,764 A | 12/1998 | Goulet et al. | 514/337 |

FOREIGN PATENT DOCUMENTS

| | | |
|---|---|---|
| EP | 1 004 585 A1 | 5/2000 |
| WO | WO 96/38438 | 12/1996 |
| WO | WO 97/14682 | 4/1997 |
| WO | WO 97/14697 | 4/1997 |
| WO | WO 97/21435 | 6/1997 |
| WO | WO 97/21703 | 6/1997 |
| WO | WO 97/21704 | 6/1997 |
| WO | WO 97/21707 | 6/1997 |
| WO | WO 97/44037 | 11/1997 |
| WO | WO 97/44041 | 11/1997 |
| WO | WO 97/44321 | 11/1997 |
| WO | WO 97/44339 | 11/1997 |
| WO | WO 98/55116 | 12/1998 |
| WO | WO 98/55119 | 12/1998 |
| WO | WO 98/55470 | 12/1998 |
| WO | WO 98/55479 | 12/1998 |
| WO | WO 99/09033 | 2/1999 |
| WO | 99/33831 | * 7/1999 |
| WO | WO 99/33831 | 7/1999 |
| WO | WO 99/51232 | 10/1999 |

OTHER PUBLICATIONS

Cho et al., "Discovery of a novel, potent, and orally active nonpeptide of the human luteinizing hormone–releasing hormone (LHRH) receptor ", *J. Med. Chem.* 41(22): 4190–4195, 1998.

\* cited by examiner

*Primary Examiner*—Mukund J. Shah
*Assistant Examiner*—Tamthom N. Truong
(74) *Attorney, Agent, or Firm*—Seed Intellectual Property Law Group PLLC

(57) ABSTRACT

GnRH receptor antagonists are disclosed which have utility in the treatment of a variety of sex-hormone related conditions in both men and women. The compounds of this invention have the structure:

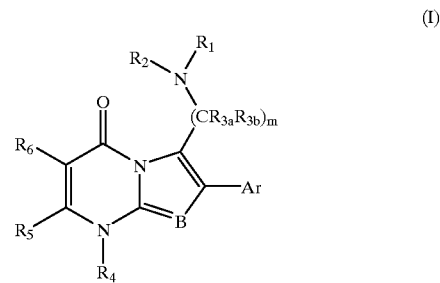

(I)

including stereoisomers, prodrugs and pharmaceutically acceptable salts thereof, wherein Ar, B, $R_1$, $R_2$, $R_{3a}$, $R_{3b}$, $R_4$, $R_5$, $R_6$ and m are as defined herein.

38 Claims, No Drawings

GONADOTROPIN-RELEASING HORMONE RECEPTOR ANTAGONISTS AND METHODS RELATING THERETO

CROSS-REFERENCE TO RELATED APPLICATIONS

This application claims the benefit of U.S. Provisional Application No. 60/219,316 filed Sep. 23, 1998; and Provisional Application No. 60/193,335 filed Jul. 28, 1999 as well as Provisional Application No. 60/287,591 filed May 11, 1999.

TECHNICAL FIELD

This invention relates generally to gonadotropin-releasing hormone (GnRH) receptor antagonists, and to methods of treating disorders by administration of such antagonists to a warm-blooded animal in need thereof.

BACKGROUND OF THE INVENTION

Gonadotropin-releasing hormone (GnRH), also known as luteinizing hormone-releasing hormone (LHRH), is a decapeptide (pGlu-His-Trp-Ser-Tyr-Gly-Leu-Arg-Pro-Gly-NH$_2$) that plays an important role in human reproduction. GnRH is released from the hypothalamus and acts on the pituitary gland to stimulate the biosynthesis and release of luteinizing hormone (LH) and follicle-stimulating hormone (FSH). LH released from the pituitary gland is responsible for the regulation of gonadal steroid production in both males and females, while FSH regulates spermatogenesis in males and follicular development in females.

Due to its biological importance, synthetic antagonists and agonists to GnRH have been the focus of considerable attention, particularly in the context of prostrate cancer, breast cancer, endometriosis, uterine leiomyoma, and precocious puberty. For example, peptidic GnRH agonists, such as leuprorelin (pGlu-His-Trp-Ser-Tyr-D-Leu-Leu-Arg-Pro-NHEt), have been used to treat such conditions. Such agonists appear to function by binding to the GnRH receptor in the pituitary gonadotropins, thereby inducing the synthesis and release of gonadotropins. Chronic administration of GnRH agonists depletes gonadotropins and subsequently down-regulates the receptor, resulting in suppression of steroidal hormones after some period of time (e.g., on the order of 2–3 weeks following initiation of chronic administration).

In contrast, GnRH antagonists are believed to suppress gonadotropins from the onset, and thus have received the most attention over the past two decades. To date, some of the primary obstacles to the clinical use of such antagonists have been their relatively low bioavailability and adverse side effects caused by histamine release. However, several peptidic antagonists with low histamine release properties have been reported, although they still must be delivered via sustained delivery routes (such as subcutaneous injection or intranasal spray) due to limited bioavailability.

In view of the limitations associated with peptidic GnRH antagonists, a number of nonpeptidic compounds have been proposed. For example, Cho et al. (*J. Med. Chem.* 41:4190–4195, 1998) discloses thieno[2,3-b]pyridin-4-ones for use as GnRH receptor antagonists; U.S. Pat. Nos. 5,780,437 and 5,849,764 teach substituted indoles as GnRH receptor antagonists (as do published PCTs WO 97/21704, 98/55479, 98/55470, 98/55116, 98/55119, 97/21707, 97/21703 and 97/21435); published PCT WO 96/38438 discloses tricyclic diazepines as GnRH receptor antagonists; published PCTs WO97/14682, 97/14697 and 99/09033 disclose quinoline and thienopyridine derivatives as GnRH antagonists; published PCTs WO 97/44037, 97/44041, 97/44321 and 97/44339 teach substituted quinolin-2-ones as GnRH receptor antagonists; and published PCT WO 99/33831 discloses certain phenyl-substituted fused nitrogen-containing bicyclic compounds as GnRH receptor antagonists.

While significant strides have been made in this field, there remains a need in the art for effective small molecule GnRH receptor antagonists. There is also a need for pharmaceutical compositions containing such GnRH receptor antagonists, as well as methods relating to the use thereof to treat, for example, sex-hormone related conditions. The present invention fulfills these needs, and provides other related advantages.

SUMMARY OF THE INVENTION

In brief, this invention is generally directed to gonadotropin-releasing hormone (GnRH) receptor antagonists, as well as to methods for their preparation and use, and to pharmaceutical compositions containing the same.

More specifically, the GnRH receptor antagonists of this invention are compounds having the following general structure (I):

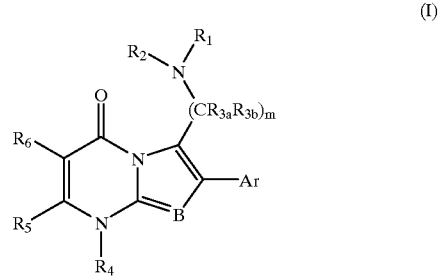

including stereoisomers, prodrugs and pharmaceutically acceptable salts thereof, wherein Ar, B, $R_1$, $R_2$, $R_{3a}$, $R_{3b}$, $R_4$, $R_5$, $R_6$ and m are as defined below.

The GnRH receptor antagonists of this invention have utility over a wide range of therapeutic applications, and may be used to treat a variety of sex-hormone related conditions in both men and women, as well as a mammal in general (also referred to herein as a "subject"). For example, such conditions include endometriosis, uterine fibroids, polycystic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization). The compounds of this invention are also useful as an adjunct to treatment of growth hormone deficiency and short stature, and for the treatment of systemic lupus erythematosis. The compounds are also useful in combination with androgens, estrogens, progesterones, and antiestrogens and antiprogestogens for the treatment of endometriosis, fibroids, and in contraception, as well as in combination with an angiotensin-converting enzyme inhibitor, an antiotensin II-receptor antagonist, or a renin inhibitor for the treatment of uterine fibroids. In addition, the compounds may be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

The methods of this invention include administering an effective amount of a GnRH receptor antagonist, preferably in the form of a pharmaceutical composition, to a mammal in need thereof. Thus, in still a further embodiment, pharmaceutical compositions are disclosed containing one or more GnRH receptor antagonists of this invention in combination with a pharmaceutically acceptable carrier and/or diluent.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as gonadotropin-releasing hormone (GnRH) receptor antagonists. The compounds of this invention have the following structure (I):

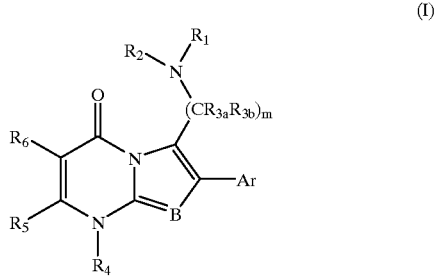

including stereoisomers, prodrugs and pharmaceutically acceptable salts thereof, wherein:

m is an integer from 1 to 6;

$R_1$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, aryl$(CR_{3c}R_{3d})_n$, substituted aryl $(CR_{3c}R_{3d})_n$, heteroaryl$(CR_{3c}R_{3d})_n$ or substituted heteroaryl$(CR_{3c}R_{3d})_n$;

$R_2$ is hydrogen, alkyl or substituted alkyl;

or $R_1$ and $R_2$ taken together with the nitrogen atom to which they are attached form a heterocycle ring or a substituted heterocycle ring;

$R_{3a}$, $R_{3b}$, $R_{3c}$ and $R_{3d}$ are the same or different and independently at each occurrence hydrogen, alkyl, substituted alkyl, hydroxy, alkoxy, thioalkyl, amino, alkylamino, dialkylamino, cyano, halogen, —C(=O) $OR_7$ or —C(=O)$NR_7R_8$;

or $R_{3a}$ and $R_{3b}$, or $R_{3c}$ and $R_{3d}$, taken together with the carbon atom to which they are attached form a carbocyclic ring or substituted carbocyclic ring;

or $R_{3a}$ and $R_1$, taken together with the carbon atom and nitrogen atom, respectively, to which they are attached form a heterocyclic ring or substituted heterocyclic ring;

$R_4$ is hydrogen, alkyl, substituted alkyl, aryl, substituted aryl, arylalkyl, substituted arylalkyl, heteroaryl, substituted heteroaryl, heteroarylalkyl or substituted heteroarylalkyl;

$R_5$ is hydrogen, halogen, cyano, alkyl, substituted alkyl, hydroxy, alkoxy, thioalkyl or mono- or di-alkylamine;

$R_6$ is hydrogen, alkyl, substituted alkyl, aryl, substituted aryl, heterocycle, substituted heterocycle, —$OR_7$, —$SR_7$, —$SOR_7$, —$SO_2R_7$, —$OSO_2R_7$, —$SO_2OR_7$, —$SO_2NR_7R_8$, —$NR_9SO_2R_7$, —C(=O)$R_7$, —C(=O)$OR_7$, —OC(=O)$R_7$, —$NR_7R_8$ —C(=O) $NR_7R_8$, —OC(=O) $NR_7R_8$, —$NR_9C(=O)R_7$, —$NR_9C(=O)$ $NR_7R_8$, —$NR_8C(=O)OR_7$ or —C(OH)$R_7R_8$;

$R_7$, $R_8$ and $R_9$ are the same or different and independently hydrogen, alkyl, substituted alkyl, aryl, substituted aryl, arylalkyl, substituted arylalkyl, heteroaryl, substituted heteroaryl, heteroarylalkyl or substituted heteroarylalkyl;

or $R_7$ and $R_8$ taken together with the nitrogen atom to which they are attached form a heterocycle ring or a substituted heterocycle ring;

n is an integer from 1 to 6; and

B and Ar are as follows:
  B is nitrogen or $CR_{10}$ when Ar is heteroaryl or substituted heteroaryl and $R_{10}$ is hydrogen; or
  B is $CR_{10}$ when Ar is aryl, substituted aryl, heteroaryl or substituted heteroaryl and $R_{10}$ is halogen, cyano, nitro, amino, mono- or di-alkylamino or alkyl.

As used herein, the above terms have the following meaning:

"Alkyl" means a straight chain or branched, noncyclic or cyclic, unsaturated or saturated aliphatic hydrocarbon containing from 1 to 8 carbon atoms, while the term "lower alkyl" has the same meaning as alkyl but contains from 1 to 4 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —$(CH_2)_2$phenyl, —$(CH_2)_3$phenyl, —CH(phenyl)$_2$, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls are pyridyl, furyl, benzofuranyl, thiophenyl, benzothiophenyl, quinolinyl, pyirolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —$CH_2$pyridinyl, —$CH_2$pyrimidinyl, and the like.

"Heterocycle" means a 5- to 7-membered monocyclic, or 7- to 10-membered bicyclic, heterocyclic ring which is either saturated, unsaturated, or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$ morpholinyl, and the like.

The term "substituted" as used herein means any of the above groups (i.e., alkyl, aryl, arylalkyl, heteroaryl, heteroarylalkyl, heterocycle and heterocyclealkyl) wherein at least one hydrogen atom is replaced with a substituent. In the case of a keto substituent ("C(=O)") two hydrogen atoms are replaced. Substituents include halogen, hydroxy, alkyl, haloalkyl, aryl, substituted aryl, arylalkyl, substituted arylalkyl, heterocycle, substituted heterocycle, heterocyclealkyl, substituted heterocyclealkyl, —NR'R", —NR'"C(=O)R' —NR'"C(=O)NR'R", —NR'"C(=O)OR'—NR'"SO$_2$R', —C(=O)R'—C(=O)OR', —C(=O)NR'R", —OC(=O)R', —OC(=O)OR', —OC(=O)NR'R" or —NR'"SO$_2$R', wherein R' and R" are the same or different and independently hydrogen, amino, alkyl, halogenated alkyl, aryl, substituted aryl, arylalkyl, substituted arylalkyl, heterocycle, substituted heterocycle, heterocylealkyl or substituted heterocyclealkyl, or wherein R' and R" taken together with the nitrogen atom to which they are attached form a heterocycle or substituted heterocycle.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

"Aryloxy" means an aryl moiety attached through an oxygen bridge (i.e., —O-alkyl) such as phenoxy and the like.

"Thiol" means —SH.

"Thioalkyl" means an alkyl moiety attached through a sulfur bridge (i.e., —S-alkyl) such as —SCH$_3$, —SCH$_2$CH$_3$ and the like.

"Thioaryl" means an aryl moiety attached through a sulfur bridge (i.e., —S-aryl) such as —S-phenyl and the like.

"Mono- or dialkylamine" means —NH(alkyl) or —N(alkyl)(alkyl), respectively.

"Sulfonylalkyl" means an alkyl moiety attached through a sulfonyl bridge (i.e., —SO$_2$-alkyl) such as —SO$_2$CH$_3$, —SO$_2$CH$_2$CH$_3$ and the like.

"Sulfonylaryl" means an aryl moiety attached through a sulfonyl bridge (i.e., —SO$_2$-aryl) such as —SO$_2$-phenyl and the like.

Depending upon the choice of the B moiety of structure (I), compounds of this invention have the following structure (II) when B is nitrogen, and the following structure (III) when B is CR$_{10}$:

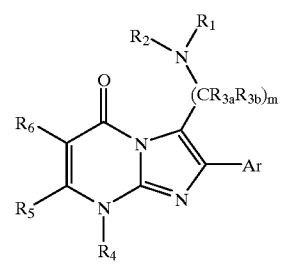

(II)

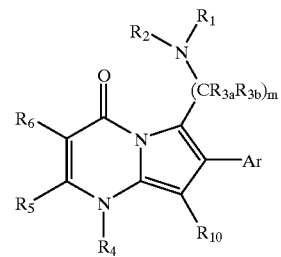

(III)

In structure (II), Ar is heteroaryl or substituted heteroaryl. Similarly, when R$_{10}$ is hydrogen in structure (III), Ar is heteroaryl or substituted heteroaryl. However, when R$_{10}$ of structure (III) is halogen, cyano, nitro, amino, mono- or di-alkylamino or alkyl, Ar is aryl, substituted aryl, heteroaryl or substituted heteroaryl.

In one embodiment, R$_6$ is —C(=O)OR$_7$, and representative compounds of this invention have the following structure (IV):

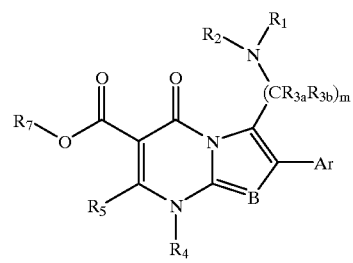

(IV)

In another embodiment, R$_6$ is —C(=O)NR$_7$R$_8$, and representative compounds of this invention have the following structure (V):

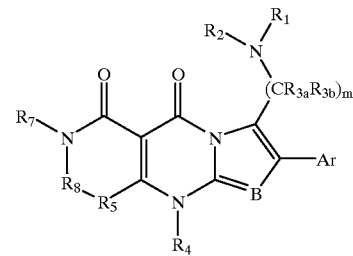

(V)

In other embodiments, R$_6$ is —C(=O)R$_7$, —C(OH)R$_7$R$_8$ or —OR$_7$, and representative compounds of this invention have the following structures (VI), (VII) and (VIII), respectively:

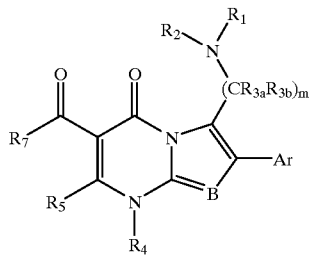
(VI)

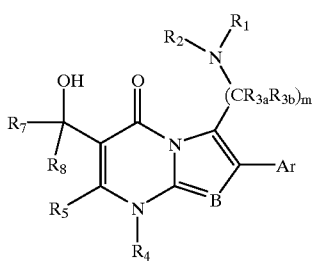
(VII)

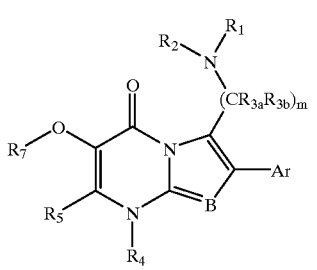
(VIII)

In still further embodiments, $R_6$ is hydrogen, alkyl, substituted alkyl, hydroxy, thioalkyl or sulfonylalkyl, and representative compounds of this invention have the following structures (IX) through (XIV), respectively:

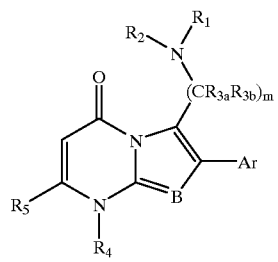
(IX)

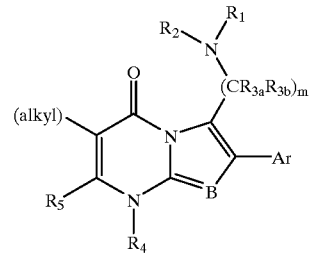
(X)

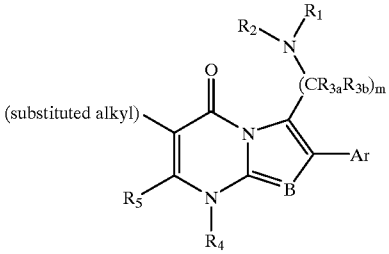
(XI)

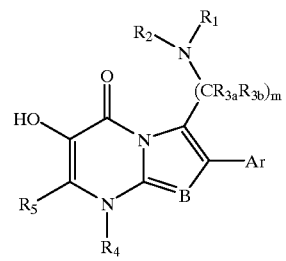
(XII)

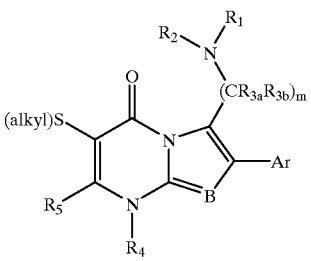
(XIII)

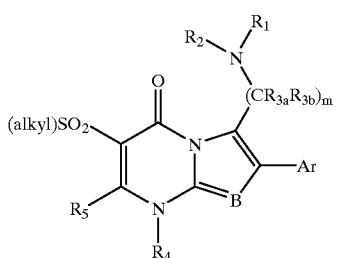
(XIV)

In one embodiment of structure (I), $R_1$ and $R_2$, taken together with the nitrogen atom to which they are attached, form a heterocycle ring as presented by the following structures (XV):

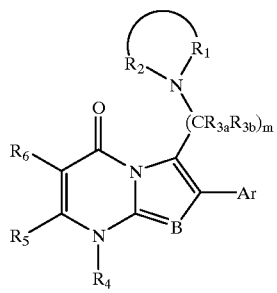
(XV)

Similarly, in more specific embodiments of structure (V), $R_7$ and $R_8$, taken together with the nitrogen atom to which they are attached, form a heterocycle ring or substituted heterocycle ring as represented by the following structure (XVI), optionally in combination with $R_1$ and $R_2$ forming a heterocycle ring or substituted heterocycle ring as represented by the following structure (XVII):

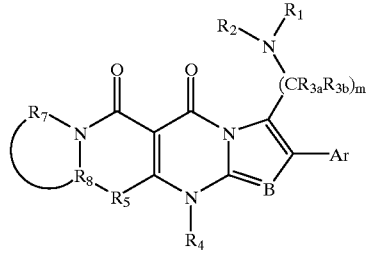

(XVI)

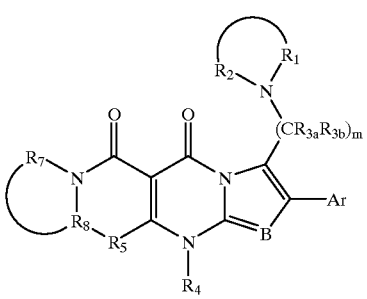

(XVII)

In another embodiment of structure (I), $R_1$ is heteroaryl $(CR_{3c}R_{3d})_n$ or substituted heteroaryl$(CR_{3c}R_{3d})_n$. In one aspect of this embodiment, the heteroaryl portion of the heteroaryl$(CR_{3c}R_{3d})_n$ moiety is pyridinyl (e.g, pyridin-2-yl), and the compounds of this invention have the following structure (XVIII):

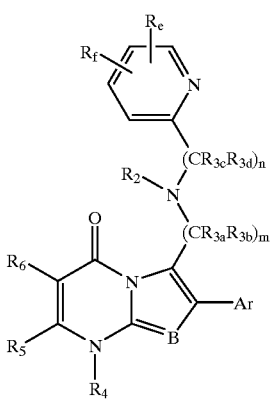

(XVIII)

wherein $R_e$ and $R_f$ are the same or different and represent optional substituents independently selected from hydrogen, alkyl, alkoxy, dialkyamino, halo and cyano.

In still a further embodiment of structure (I), the $(CR_{3a}R_{3b})_m$ moiety is an alkilidene moiety, as represented by the following structure (XIX):

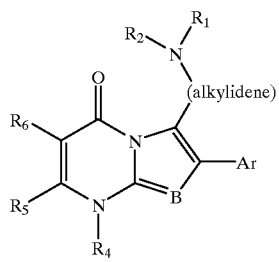

(XIX)

wherein alkylidene means a bivalent alkyl radical, including bivalent straight chain alkyls such as methylene (i.e., —CH$_2$—), ethylene (i.e., —CH$_2$CH$_2$—), and the like, bivalent branched alkyls such as —CH(CH$_3$)—, —C(CH$_3$)$_2$—, and the like, and bivalent cycloalkyls such as cyclohexylene, and the like.

In more specific embodiments of this invention, the Ar moiety is a heteroaryl moiety, as represented by the following structure (XX):

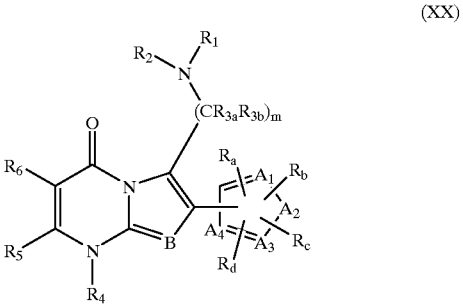

(XX)

wherein $A_1$, $A_3$ and $A_4$ are the same or different and independently nitrogen or CH;

$A_2$ is oxygen, sulfur, NH, N=N or N=CH; and $R_a$, $R_b$, $R_c$ and $R_d$ are optional substituents that are the same or different and independently halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, hydroxy, alkoxy, aryloxy, thiol, thioalkyl, thioaryl, sulfonylalkyl, sulfonylaryl, amino, mono- or di-alkylamino, mono- or di-arylamino, —COOalkyl, —COOaryl, —CONHalkyl, —CONHaryl, —CON(alkyl)$_2$, —CON(aryl)$_2$, —NHCOalkyl, —NHCOaryl, —N(alkyl)COalkyl, —N(alkyl)COaryl, —NHSO$_2$alkyl, —NHSO$_2$aryl, N(alkyl)SO$_2$alkyl, —N(alkyl)SO$_2$aryl, —NHCONHalkyl or —NHCONHaryl;

or $R_a$ and $R_b$ taken together with the atoms to which they are attached form aryl, substituted aryl, heteroaryl or substituted heteroaryl.

Accordingly, depending upon the choice of $A_1$, $A_2$, $A_3$ and $A_4$ in structure (XX), the heterocyclic ring containing $A_1$, $A_2$, $A_3$ and $A_4$ includes the following heteroaryls:

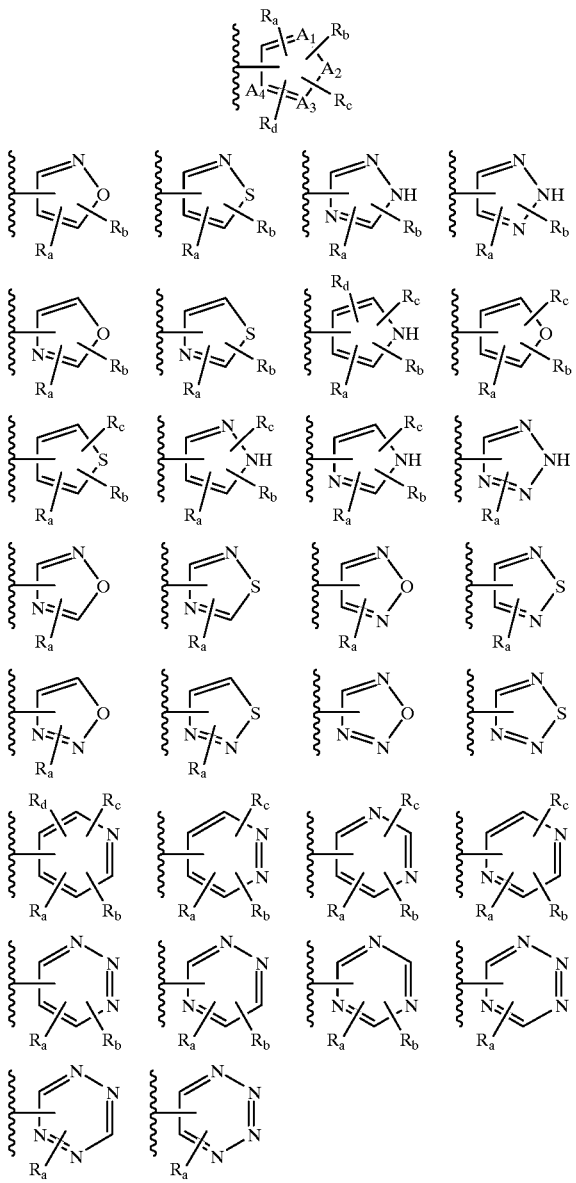

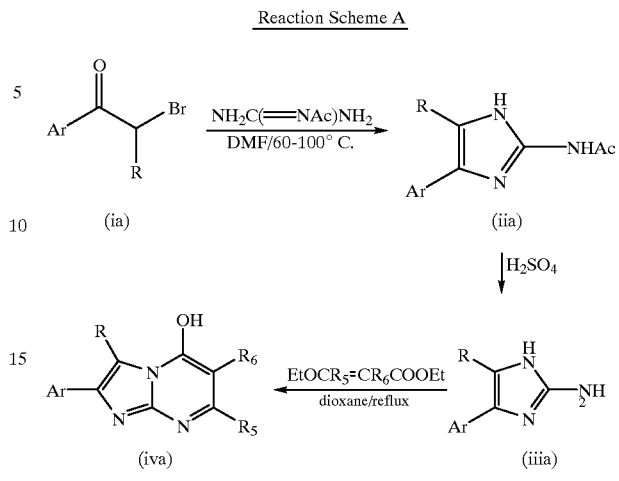

Reaction Scheme A

As shown in Reaction Scheme A, imidazolo[1,2-a]pyrimidone (iva) can be prepared from alpha-bromoheteroaryl ketone (R=alkyl). Thus, cyclization of bromoketone (ia) with acetyl guanidine in an appropriate solvent such as dimethylformamide at a temperature of 25–120° C. for a period of 1–72 hours to give 2-acetamidoimidazole (iia), which can be hydrolyzed with an acid such as sulfuric acid in an appropriate solvent such as water or ethanol at a temperature of 60–120° C. for a period of 2–24 hours to give 2-aminioimidazole (iiia). 2-Aminoimidazole (iiia) can be modified by cyclization with substituted acrylate in an inert solvent such as methanol, dioxane or phenylether at a temperature of 60–260° C. for a period of 0.5–16 hours to give imidazolo[1,2-a]pyrimidone (iva).

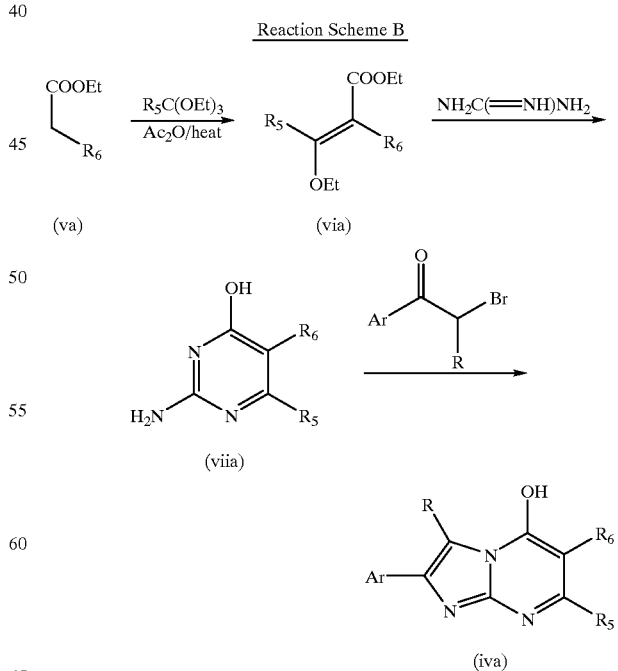

Reaction Scheme B

In addition to the above heteroaryls, this invention also includes heteroaryls wherein $R_a$ and $R_b$ taken together with the atoms to which they are attached form aryl or heteroaryl, including (but not limited to) benzofuranyl, isobenzofuranyl, thionaphthenyl, isothionaphthenyl, indoyl, purinyl, quinolinyl, isoquinolinyl, pyrano[3,4-b]pyrrolyl, indoxazinyl, benzoxazolyl, anthranyl, cinnolinyl, quinazolinyl, naphthy fidinyl, prido[3,4-b]pyridinyl, pyrido[3,2-b]pyridinyl, pyrido[4,3-b]pyridinyl, and the like.

The compounds of the present invention may be prepared by known organic synthesis techniques, including the methods described in more detail in the Examples. In general, however, the compounds of structure (II) may be made by the following Reaction Schemes A and B, and the compounds of structure (III) by Reaction Schemes C and D. Reaction Schemes E through M illustrate further synthetic procedures applicable to compounds of structure (I) generally. In the following reaction schemes, all substituents are as defined above unless indicated otherwise.

Alternatively, imidazolo[1,2-a]pyrimidone (iva) may be prepared according to Reaction Scheme B by condensation of 2-aminopyrimidine (viia) with the alpha-bromoheteroaryl ketone (ia) in the presence of a base such as sodium hydride, tetrabutylammonium fluoride, potassium carbonate in a inert solvent such as DME, dimethylformamide, ethanol at a temperature of 25–100° C. for a period of 12–24 hours.

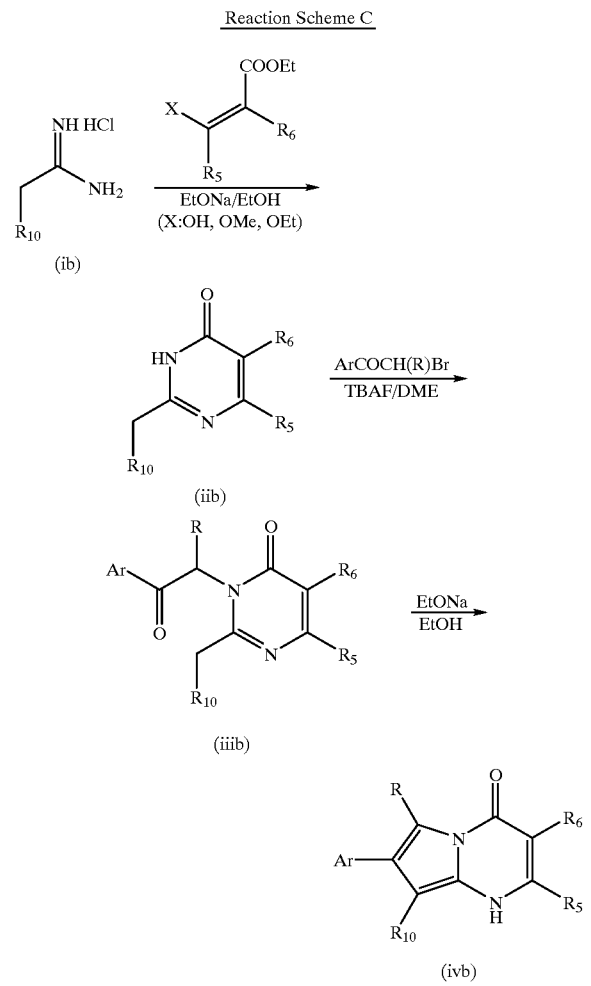

In Reaction Scheme C, cyclization of amidine hydrochloride (ib) with a bis-electrophilic reagent, such as diethyl ethoxymethylene malonate in an organic solvent such as ethanol, in the presence of sodium ethoxide at a temperature of 25–100° C., preferably at reflux in ethanol, for a period of 2–12 hours, gives the corresponding pyrimidone (iib). The pyrimidone (iib) may be alkylated by treatment with a base such as tetrabutylamonium fluoride, sodium hydride, or sodium ethoxide in an inert solvent such as 1,2-demethoxyethane, tetrahydrofuran, or mixtures thereof at 0–25° C. for a period of 30 minutes, followed by an alpha-bromoketone at 0–25° C. for 12–24 hours to provide the alkylated pyrimidone (iiib). The pyrimidone (iiib) may be cyclized upon treatment with a strong base such as sodium ethoxide, sodium hydride or LiN(SiMe$_3$)$_2$ in an inert solvent such as ethanol at 25–80° C. for 2–4 hours to give the pyrrolo[1,2-a]pyrimidone (ivb).

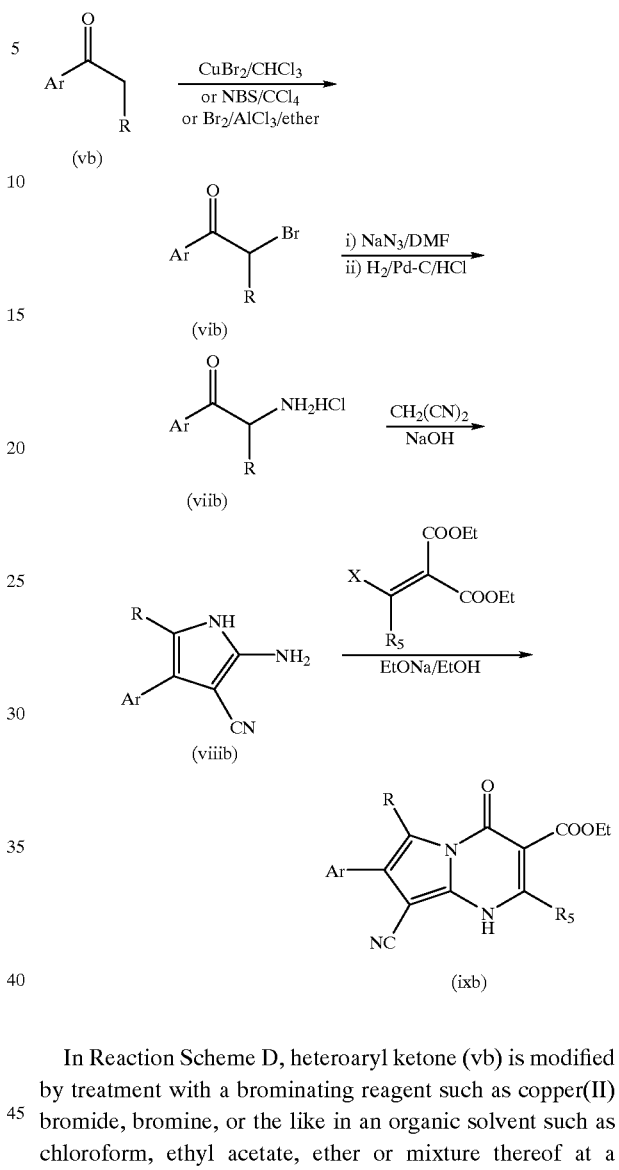

In Reaction Scheme D, heteroaryl ketone (vb) is modified by treatment with a brominating reagent such as copper(II) bromide, bromine, or the like in an organic solvent such as chloroform, ethyl acetate, ether or mixture thereof at a temperature of 25–100° C., preferably at reflux in a mixture of chloroform and ethyl acetate, for a period of 2–12 hours gives the corresponding alpha-bromoketon (vib). Alternatively, heteroaryl ketone (vb) may be treated with N-bromosuccinamide, or bromine in an inert solvent such as carbon tetrachloride or chloroform with a radical initiator such as AIBN, at reflux to give the bromoketone (vib). The bromoketone (vib) is substituted by treatment with a azide salt such sodium azide, potassium azide or the like in an inert solvent such as DMF, tetrahydrofuran, ether, water or mixture thereof at 0–50° C. for a period of 2–12 hours. The azido group is converted to an amino group when it is dissolved in an appropriate solvent, such a ethanol or methanol with hydrochloric acid, and (a) to the solution is added palladium-carbon or Raney Nickel as the catalyst and the mixture is reacted at room temperature for one to 12 hours under hydrogen atmosphere, or (b) to the solution is added triethyl phorsphite and the mixture is reacted at 0–25° C. for 1–24 hours to provide the amino ketone hydrochloride (viib). The amino ketone (viib) is cyclized with malononitrile upon treatment with a strong base such as sodium hydroxide or potassium hydroxide in an inert solvent such as acetonitrile, water, ethanol or mixture thereof at 25–100° C. for 2–24 hours to give the aminopyrrole (viiib). The aminopyrrole (viiib) is condensed with a biselectrophilic reagent such as diethyl ethoxymethylenemalonate in an inert solvent such as ethanol or dioxane at a temperature of 25–100° C. for 12–24 hours, then cyclized in a high boiling solvent such as phenyl ether at 200–265° C. for 0.5–2 hours to provide pyrrolo[1,2-a]pyrimidone (ixb).

Reaction Scheme E

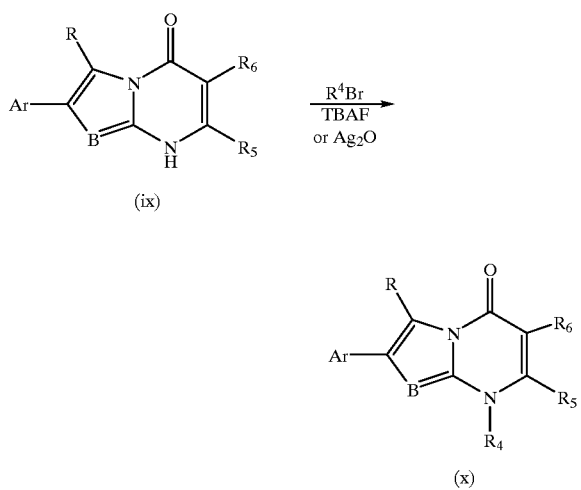

(ix)

(x)

As shown in Reaction Scheme E, intermediate (ix) can be modified by treatment with an alkyl halide in the presence of a base such as tetrabutylamonnium fluoride, sodium hydride or silver(I) oxide in an inert solvent such as DMF, DME, THF or the like at 25–80° C. for a period of 1–72 hours to give the corresponding 4-substituted intermediate (x). Alternatively, compound (x) can also be prepared by a Mitsunobu coupling reaction of the starting material (ix) with an alcohol and a coupling reagent such as a mixture of diethyl azodicarboxylate and triphenylphosphine in an inert solvent such as tetrahydrofuran, benzene or ether at a temperature of 0–100° C. for 1–24 hours.

Reaction Scheme F

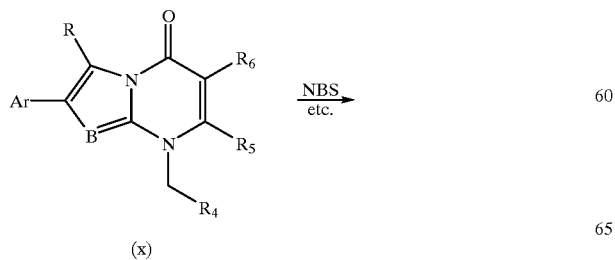

(x)

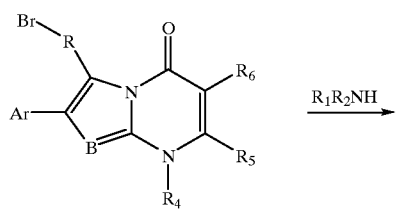

(xi)

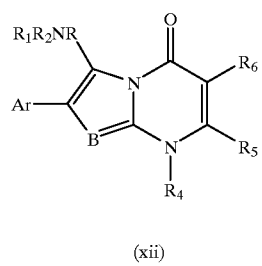

(xii)

As shown in Reaction Scheme F, intermediate (x) (R is an alkyl group) can be modified by treatment with a brominating reagent such as N-bromosuccinnamide, in the presence of a radical initiator such as AIBN or benzoyl peroxide, in an inert solvent such as carbon tetrachloride, chloroform at temperature ranging from 25 –100° C. for a period of 1–24 hours to give the corresponding bromoalkyl intermediate (xi)m which is reacted with a primary or secondary amine (1–5 eq) at a temperature ranging from 0 to 50° C. for a period of 0.5 to 16 hours to give compound (xii). The reaction can be carried out under stirring in an appropriate solvent such as dimethylformamide, acetonitrile, ethanol, tetrahydrofuran, chloroform or carbon tetrachloride. In this reaction, if necessary, a base such triethylamine, DBU or pyridine may be used.

Reaction Scheme G

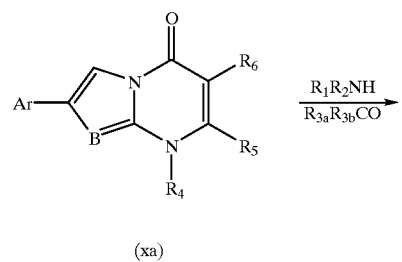

(xa)

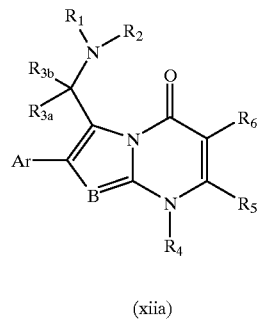

(xiia)

As shown in Reaction Scheme G, intermediate (xa) can be modified by treatment with an amine such as alkylamine or dialkylamine and an aldehyde such as formaldehyde, paraformaldehyde or acetaldehyde in an appropriate solvent such as ethanol, chloroform, dioxane, acetic acid, or acetonitrile, at a temperature of 25–100° C. for a period of 0.5–16 hours to give the amine analog (xiia).

Reaction Scheme H

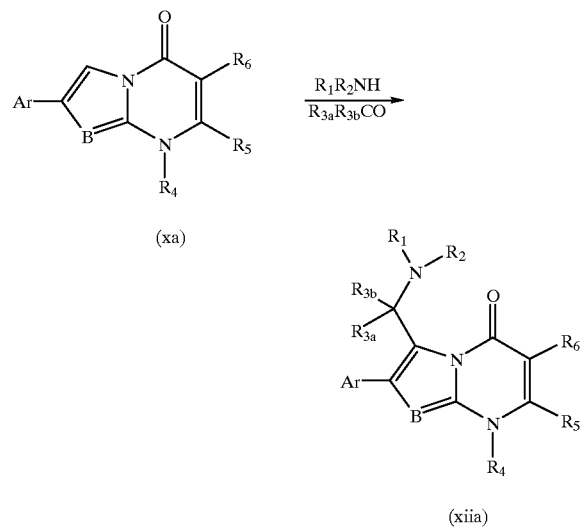

As shown in Reaction Scheme H, the ethyl ester of intermediate (xiii) can be converted to another ester (xiv) by treatment with an excess of alcohol ($R_7OH$) and a strong base such as butyllithium, $LiN(SiMe_3)_2$, LDA or potassium t-butoxide with or without an inert solvent such as dioxane, tetrahydrofuran or dimethylformamide, at a temperature of 25–100° C. for a period of 0.5–16 hours. The ethyl ester group of compound (xiii) can also be converted to an amide group by dissolving the starting material in an appropriate solvent (e.g., dichloromethane or dichloroethane) and adding to a mixture of a primary or secondary amine ($R_7R_8NH$) and triethylaluminum or dibutylaluminum hydride, and the mixture reacted at 20–100° C. for 1–12 hours under nitrogen atmosphere to give amide analog (xv). The ester group of compound (xiii) can also be converted to ketone (xvi) when the starting material is reacted with an appropriate organometallic reagent such as alkyl lithium ($R_7Li$), alkylmagnesiumhalide or organozinc, in an inert solvent such as tetrahydrofuran, ether, hexanes or mixture thereof at a temperature of 0–25° C. for a period of 1–16 hours. Furthermore, when more organometalic reagent ($R_8Li$) is used to react with ketone (xvi), the corresponding alcohol (xvii) is obtained.

Reaction Scheme I

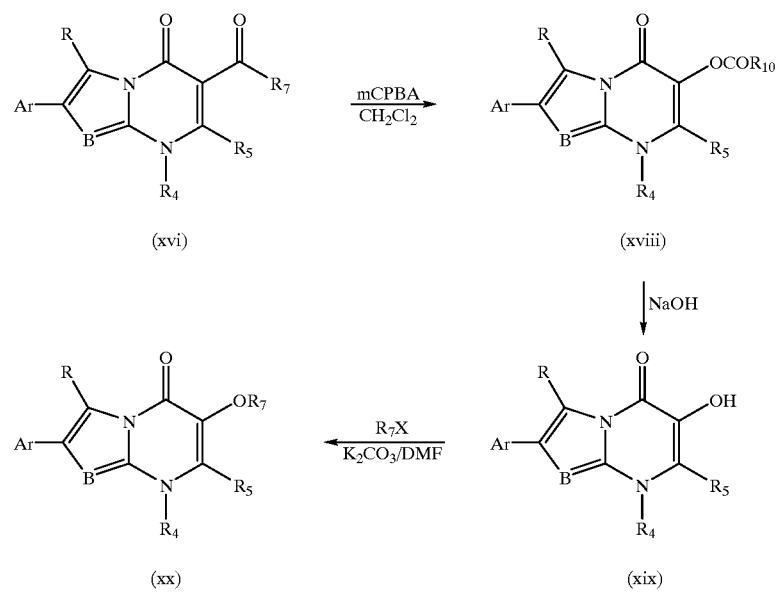

As shown in Reaction Scheme I, the ketone derivative of compound (xvi) may be oxidized to provide the carboxylic ester analog (xviii), by treatment with an oxidation reagent such as m-chloroperbenzoic acid in an appropriate solvent such as dichloromethane, tetrahydrofuran, ethyl acetate or the like for a period of 1–16 hours or until the starting material has been consumed. The ester (xviii) can hydrolyzed to the corresponding hydroxy compound (xix) by treatment with a base such as sodium hydroxide, lithium hydroxide or the like in an appropriate solvent such as ethanol, water, tetraydrofuran, or mixture thereof at a temperature of 25–100° C. for a period of 2–24 hours. The ether derivative (xx) can be prepared by treatment of (xix) with an alkyl halide ($R_7X$) and a base such as potassium carbonate or sodium hydroxide in an inert organic solvent such as acetone, dimethylformamide or DMSO at a temperature of 25–100° C. for a period of 1–72 hours to give product (xx).

starting compound (xxi) is dissolved in an appropriate solvent, (e.g. ethanol or methanol), and (a) to the solution is added a catalyst such as palladium-carbon or Raney nickel, and the mixture is reacted at room temperature for one to 12 hours under hydrogen atmosphere, or (b) to the solution is added iron powder and hydrochloric acid, and the mixture is reacted at room temperature for one to 12 hours, to give the amino compound (xxii). Mono- or dialkylamino analogs (xxiii and xxiv) can be prepared by reductive amination of amino compound (xxii) with an aldehyde and a reducing agent such as sodium cyanoborohydride, sodium borohydride in an appropriate solvent such as acetic acid, ethanol, acetonitrile, water or mixture thereof at a temperature 0–100° C. for a period of 1–24 hours. Alternatively, (xxiii) and (xxiv) can be prepared by treatment of (xxii) with an alkyl halide and a base such as sodium hydride, potassium carbonate or sodium methoxide in an inert solvent such as Reaction Scheme J

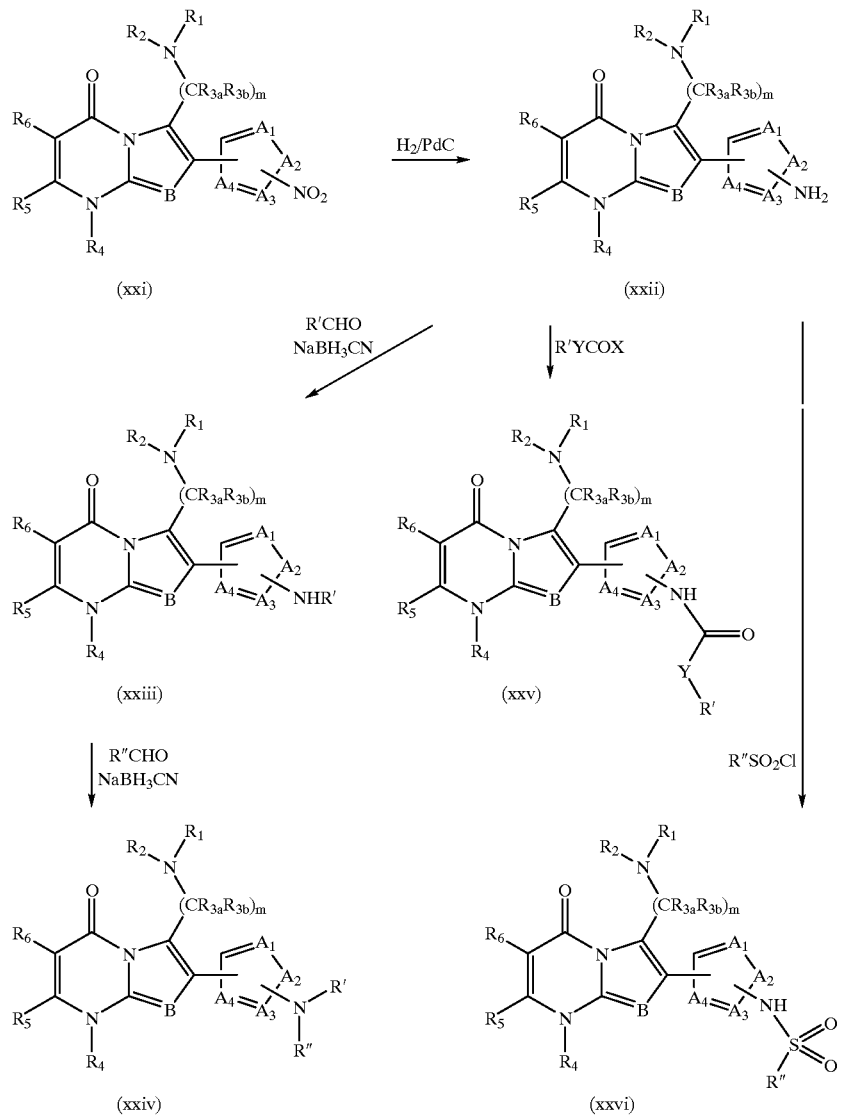

As shown in Reaction Scheme J, the nitro group as the substituent can be converted to an amino group when the tetrahydrofuran, dimethylformamide or DMSO for a temperature of 25–100° C. for a period of 2–24 hours.

Urea derivatives (xxv) can be prepared by treatment of amine (xxii) with carbamoyl chloride (R'YCOX, Y=NR", X=Cl), or an alternatively with an isocyanate regent, and an amine base, such as pyridine, triethylamine, diisopropylethylamine, N-methylmorpholine or the like, in an inert solvent, such as dichloromethane, chloroform, tetrahydrofuran or mixture thereof at a temperature of 0–65° C. for a period of 1–72 hours. Compound (xxii) can also be modified by treatment with a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as dichloromethane, chloroform, terahydrofuran, or the like at a temperature of −20 to 0° C. for a period of 0.5–16 hours. After this time, the reaction mixture is treated with an appropriate mono- or disubstituted amine at −20 to 25° C. for a period of 1–16 hours to give the urea analog (xxv).

The amino analog (xxii) can also be modified by acylation under a variety of conditions. For example, treatment of (xxii) with an acid chloride (R'YCOX, Y=CH$_2$, X=Cl), acid anhydride, active ester, or alkyl chloroformate (R'YCOX, Y=O, X=Cl) and an amine base such as triethylamine, diisopropylethylamine, pyridine, or the like in an inert solvent such as dichloromethane, chloroform, tetrahydrofuran, ethyl acetate, or mixture thereof at 0° C. to room temperature for a period of one to 12 hours gives the corresponding amide/urethane derivative (xxv). Alternatively (xxii) may be coupled with carboxylic acid promoted by a dehydrating reagent such as 1,3-dicyclohexylcarbodiimide (DCC) or 1-(3-dimethylaminopropyl)-3-ethylcarbodiimide hydrochloride (EDC), with or without a tertiary amine base such as pyridine or diisopropylethylamine in an inert solvent such as dichloromethane, chloroform, demethylformamide, or the like at room temperature for a period of 2–24 hours to provides the corresponding amide (xxv).

The amino compound (xxii) can also be modified by treatment with appropriate sulfonyl chloride or sulfamyl chloride with an amine base such as pyridine or triethylamine in an inert solvent such as dichloromethane, chloroform or tetrahydrofuran at a temperature of −20 to 25° C. for a period of 0.5 to 12 hours to give the corresponding N-sulfonamide or N-sulfamylamide derivatives (xxvi).

Reaction Scheme K

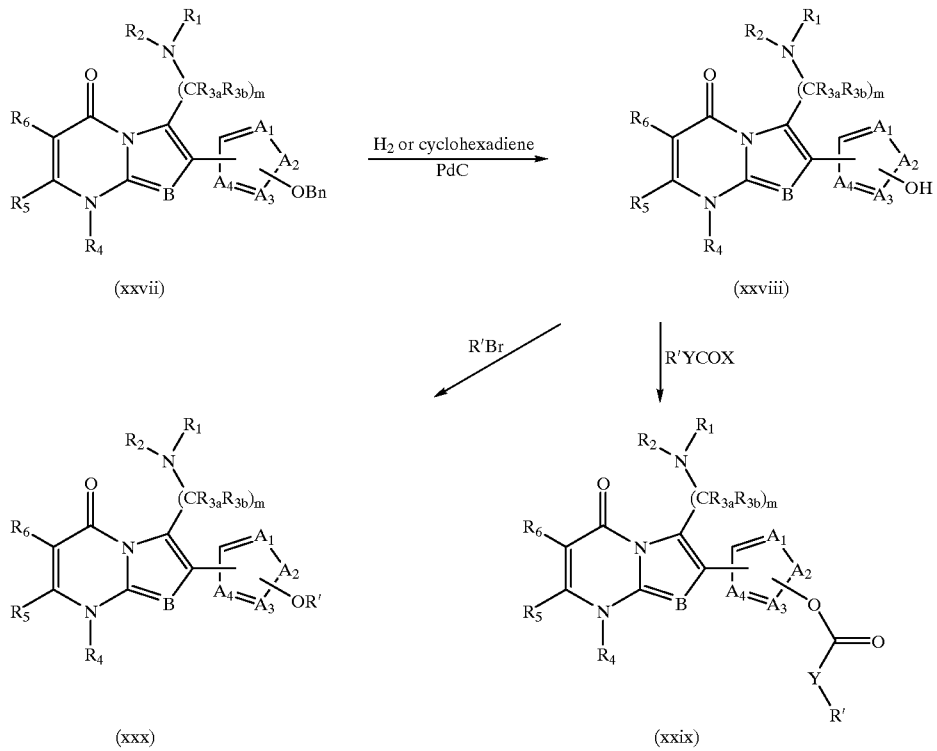

As shown in reaction Scheme K, the benzyloxy analog (xxvii) can be converted to the hydroxy compound (xxviii) by treatment with a catalyst such as palladium-carbon or Raney nickel in an inert solvent such as ethanol, methanol or ethyl acetate, on mixture thereof under hydrogen atmosphere at room temperature for a period of 1–24 hours. The hydroxy compound (xxviii) can be further modified to another analog (xxix) by treatment with an acid chloride, acid anhydride, alkyl chloroformate, mono-alkyl or dialkylamino carbonyl chloride and an amine base such as triethylamine, pyridine, or N-methylmorpholine in an inert solvent such as dichloromethane, chloroform, ethyl acetate, or tetrahydrofuran at 0 to 65° C. for a period of 1–12 hours to give (xxix). The hydroxy compound (xxviii) can also be modified to ether (xxx) by treatment with an alkyl or substituted halide and a base such as potassium carbonate in an inert solvent such as acetone, acetonitrile, or dimethylformamide at 25–100° C. for a period of 12–72 hours.

Reaction Scheme L

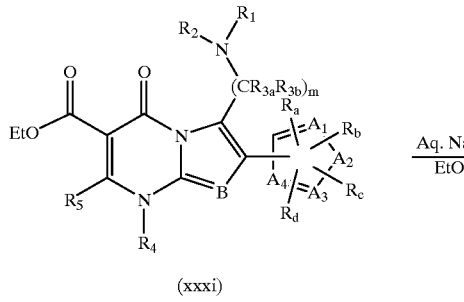

(xxxi)

Aq. NaOH
EtOH

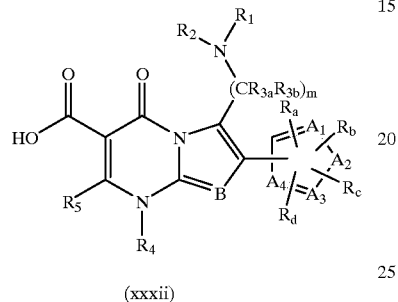

(xxxii)

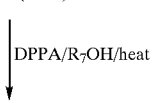

DPPA/R₇OH/heat

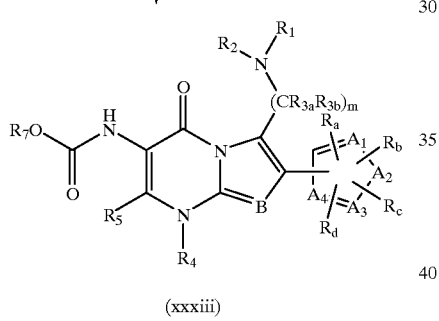

(xxxiii)

As shown in Scheme L the ethyl ester (xxxi) can be hydrolyzed to the corresponding acid analog (xxxii) by treatment of the ester (xxxi) with a base such as sodium hydroxide, lithium hydroxide or potassium carbonate in an aqueous solvent such as ethanol, methanol, tetrahydrofuran, water or mixture thereof at 0–100° C. for 1–24 hours. The acid (xxxii) can be modified by treatment with diethyl azido phosphorate (DPPA) and a base such as triethylamine in the presence of an alcohol (R₇OH) in an inert solvent such as toluene, dioxane or dimethylformamide at a temperature of 25–120° C. for a period of 1–24 hours to give the carbamate (xxxiii).

Reaction Scheme M

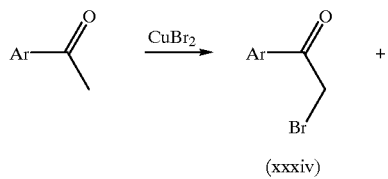

(xxxiv)

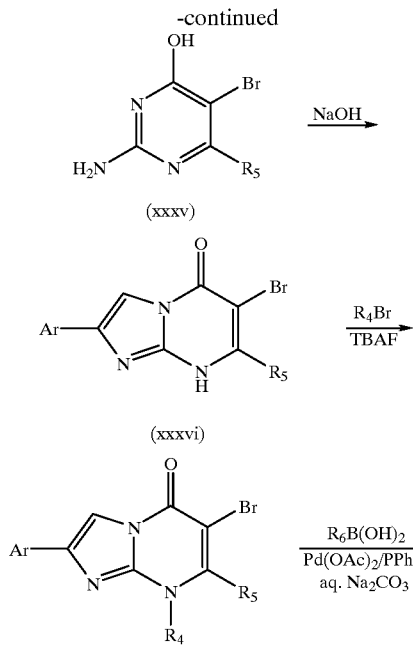

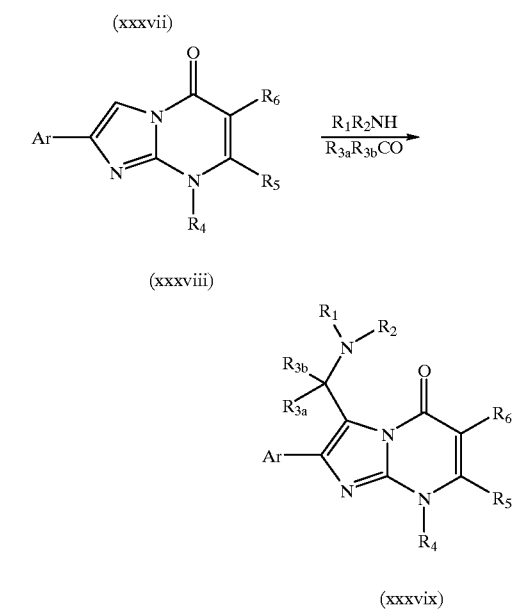

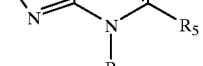

(xxxvix)

As shown in Reaction Scheme M, compounds of structure (II) may be made by conversion of the appropriate aceto-heteroaryl to bromoacetal (xxxiv), which is then reacted with 2-amino-5-bromo-6-methylpyrimidin-4-ol (xxxv) to give the corresponding imidazolopyrimid-4-one (xxxvi). Compound (xxxvi) is then converted to the R₄-substituted compound (xxxvii) followed by R₆-substituted compound (xxxviii), which is then utilized to form compound (xxxvix). This reaction may also be employed for compounds of structure (III), after formation of the corresponding intermediate (xxxvi) via Reaction Scheme C.

Representative GnRH receptor antagonists of this invention include the following compounds (a) through (p):

(a) 2-(2,5-Dimethylfuran-3-yl)-3-[N-methyl-(2-pyridylethyl)]aminomethyl-5-(3-pentoxycarbonyl)-7-(2-fluorobenzyl)imidazolo[1,2-a]pyrimid-4-one;

(b) 2-(1-Methylpyrrol-3-yl)-3-{N-[2-(2-pyridyl)ethyl]-N-methylaminomethyl}-5-(3-methoxyphenyl)-6-methyl-7-(2-fluorophenylmethyl)imidazolo[1,2-a]pyrimid-4-one;

(c) 2-(Thiophen-2-yl)-3-{N-[2-(2-pyridyl)ethyl]-N-methylaminomethyl}-5-(3-methoxyphenyl)-6-methyl-7-(2-fluorophenylmethyl)imidazolo[1,2-a]pyrimid-4-one;

(d) 2-(2,5-Dimethylfur-3-yl)-3-{N-[2-(2-pyridyl)ethyl]-N-methylaminomethyl}-5-(3-methoxyphenyl)-6-methyl-7-(2-fluorophenylmethyl)imidazolo[1,2-a]pyrimid-4-one;

(e) 2-(Pyrid-3-yl)-3-{N-[2-(2-pyridyl)ethyl]-N-methylaminomethyl}-5-(3-methoxyphenyl)-6-methyl-7-(2-fluorophenylmethyl)imidazolo[1,2-a]pyrimid-4-one;

(f) (1-[N-Methyl-(2-pyridylethyl)]aminomethyl-2-(2,5-dimethylfuran-3-yl)-4-(2-fluorobenzyl)-6-(3-pentoxycarbonyl)pyrrolo[1,2-a]pyrimid-7-one;

(g) 1-[N-Methyl-(2-pyridylethyl)]aminomethyl-2-(4-methoxyphenyl)-3-cyano-4-(2-fluorobenzyl)-6-ethoxycarbonylpyrrolo[1,2-a]pyrimid-7-one;

(h) 1-(N-Benzyl-N-methyl)aminomethyl-2-(4-methoxyphenyl)-3-cyano-4-(2-fluorobenzyl)-6-ethoxycarbonylpyrrolo[1,2-a]pyrimid-7-one;

(i) 1-(N-Benzyl-N-methyl)aminomethyl-2-(4-methoxyphenyl)-3-cyano-4-(2-cyanobenzyl)-6-ethoxycarbonylpyrrolo[1,2-a]pyrimid-7-one;

(j) 1-(N-Benzyl-N-methyl)aminomethyl-2-(4-methoxyphenyl)-3-cyano-4-(2-methoxybenzyl)-6-ethoxycarbonylpyrrolo[1,2-a]pyrimid-7-one;

(k) 1-(N-Benzyl-N-methyl)aminomethyl-2-(4-methoxyphenyl)-3-cyano-4-(2,4-difluorobenzyl)-6-ethoxycarbonylpyrrolo[1,2-a]pyrimid-7-one;

(l) 1-(N-Benzyl-N-methyl)aminomethyl-2-(4-isobutoxyphenyl)-3-cyano-4-(2-fluorobenzyl)-6-ethoxycarbonylpyrrolo[1,2-a]pyrimid-7-one;

(m) 1-[N-Methyl-(2-pyridylethyl)]aminomethyl-2-(2,5-dimethylfuran-3-yl)-4-(2-fluorobenzyl)-6-(3-pentoxycarbonyl)pyrrolo[1,2-a]pyrimid-7-one;

(n) 1-[N-Methyl-(2-pyridylethyl)]aminomethyl-2-(2,5-dimethylfuran-3-yl)-4-(2-fluorobenzyl)-6-(3-pentoxycarbonyl)imidazolo[1,2-a]pyrimid-7-one;

(o) 1-(N-Benzyl-N-methyl)aminomethyl-2-(4-isobutoxyphenyl)-3-fluoro-4-(2-fluorobenzyl)-6-ethoxycarbonylpyrrolo[1,2-a]pyrimid-7-one; and (p) 1-[N-Methyl-(2-pyridylethyl)]aminomethyl-2-(4-isobutoxyphenyl)-3-fluoro-4-(2-fluorobenzyl)-6-ethoxycarbonylpyrrolo[1,2-a]pyrimid-7-one.

The compounds of the present invention may generally be utilized as the free base. Alternatively, the compounds of this invention may be used in the form of acid addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Thus, the term "pharmaceutically acceptable salt" of structure (I) is intended to encompass any and all acceptable salt forms.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol and amine functional groups of the compounds of structure (I). Further, in the case of an carboxylic acid (—COOH), esters may be employed, such as methyl esters, ethyl esters, and the like.

With regard to stereoisomers, the compounds of structure (I) may have chiral centers and may occur as recemates, reacemic mixtures and as individual enantiomers or diastereomers. All such isomeric forms are included within the present invention, including mixtures thereof. Furthermore, some of the crystalline forms of the compounds of structure (I) may exist as polymorphs, which are included in the present invention. In addition, some of the compounds of structure (I) may also form solvates with water or other organic solvents. Such solvates are similarly included within the scope of this invention.

The effectiveness of a compound as a GnRH receptor antagonist may be determined by various assay methods. Suitable GnRH antagonists of this invention are capable of inhibiting the specific binding of GnRH to its receptor and antagonizing activities associated with GnRH. For example, inhibition of GnRH stimulated LH release in immature rats may be measured according to the method of Vilchez-Martinez (*Endocrinology* 96:1130–1134, 1975). Briefly, twenty-five day old male Sprague-Dawley rats are administered an GnRH antagonist in saline or other suitable formulation by oral gavage, sub-cutaneous injection, or intravenous injection. This is followed by sub-cutaneous injection of 200 ng GnRH in 0.2 mL saline. Thirty minutes after the last injection, the animals are decapitated and trunk blood collected. After centrifugation, the separated plasma is stored at –200° C. until determination of the LH and FSH by radioimmmunoassay. Other techniques for determining the activity of GnRH receptor antagonists are well known in the field, such as the use of cultured pituitary cells for measuring GnRH activity (Vale et al., *Endocrinology* 91:562–572, 1972), and a technique for measuring radioligand binding to rat pituitary membranes (Perrin et al., *Mol. Pharmacol.* 23:44–51, 1983).

Activity of GnRH receptor antagonists are typically calculated from the $IC_{50}$ as the concentration of a compound necessary to displace 50% of the radiolabeled ligand from the GnRH receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973). GnRH receptor antagonists of this invention have a $K_i$ of 10 μM or less. In a preferred embodiment of this invention, the GnRH receptor antagonists have a $K_i$ of less than 1 μM, and more preferably less than 100 nM.

The compounds of this invention are more resistant to metabolic enzymes, provide increased bioavailability and longer duration of action, are better absorbed, are more potent, and/or have enhanced solubility properties compared to existing GnRH receptor antagonists. As GnRH receptor antagonists, the compounds of this invention have utility over a wide range of therapeutic applications, and may be used to treat a variety of sex-hormone related conditions in both men and women, as well as mammals in general. For example, such conditions include endometriosis, uterine fibroids, polycysic ovarian disease, hirsutism, precocious puberty, gonadal steroid-dependent neoplasia such as cancers of the prostate, breast and ovary, gonadotrophe pituitary adenomas, sleep apnea, irritable bowel syndrome, premenstrual syndrome, benign prostatic hypertrophy, contraception and infertility (e.g., assisted reproductive therapy such as in vitro fertilization).

The compounds of this invention are also useful as an adjunct to treatment of growth hormone deficiency and short stature, and for the treatment of systemic lupus erythematosis.

In addition, the compounds are useful in combination with androgens, estrogens, progesterones, and antiestrogens and antiprogestogens for the treatment of endometriosis, fibroids, and in contraception, as well as in combination with an angiotensin-converting enzyme inhibitor, an antiotensin II-receptor antagonist, or a renin inhibitor for the treatment of uterine fibroids. The compounds may also be used in combination with bisphosphonates and other agents for the treatment and/or prevention of disturbances of calcium, phosphate and bone metabolism, and in combination with estrogens, progesterones and/or androgens for the prevention or treatment of bone loss or hypogonadal symptoms such as hot flashes during therapy with a GnRH antagonist.

In another embodiment of the invention, pharmaceutical compositions containing one or more GnRH receptor antagonists are disclosed. For the purposes of administration, the compounds of the present invention may be formulated as pharmaceutical compositions. Pharmaceutical compositions of the present invention comprise a GnRH receptor antagonist of the present invention and a pharmaceutically acceptable carrier and/or diluent. The GnRH receptor antagonist is present in the composition in an amount which is effective to treat a particular disorder—that is, in an amount sufficient to achieve GnRH receptor antagonist activity, and preferably with acceptable toxicity to the patient. Typically, the pharmaceutical compositions of the present invention may include a GnRH receptor antagonist in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GnRH receptor antagonist, diluents, dispersing and surface active agents, binders, and lubricants. One skilled in this art may further formulate the GnRH receptor antagonist in an appropriate manner, and in accordance with accepted practices, such as those disclosed in *Remington's Pharmaceutical Sciences,* Gennaro, Ed., Mack Publishing Co., Easton, Pa. 1990.

In another embodiment, the present invention provides a method for treating sex-hormone related conditions as discussed above. Such methods include administering of a compound of the present invention to a warm-blooded animal in an amount sufficient to treat the condition. In this context, "treat" includes prophylactic administration. Such methods include systemic administration of a GnRH receptor antagonist of this invention, preferably in the form of a pharmaceutical composition as discussed above. As used herein, systemic administration includes oral and parenteral methods of administration. For oral administration, suitable pharmaceutical compositions of GnRH receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the GnRH receptor antagonist, buffers, antioxidants, bacteriostats, and other additives commonly employed in such solutions.

The compounds of this invention may be evaluated as GnRH receptor antagonists according to the following techniques.

Rat Anterior Pituitary Cell Culture Assay of GnRH Antagonists

Anterior pituitary glands are collected from 7-week-old female Sprague-Dawley rats and the harvested glands digested with collagenase in a dispersion flask for 1.5 hr at 37° C. After collagenase digestion, the glands are further digested with neuraminidase for 9 min at 37° C. The digested tissue is then washed with 0.1% BSA/McCoy's 5A medium, and the washed cells suspended in 3% FBS/0.1 BSA/McCoy's 5A medium and plated into 96-well tissue culture plates at a cell density of 40,000 cells per well in 200 $\mu$l medium. The cells are then incubated at 37° C. for 3 days. One pituitary gland normally yields one 96-well plate of cells, which can be used for assaying three compounds. For assay of an GnRH antagonist, the incubated cells are first washed with 0.1% BSA/McCoy's 5A medium once, followed by addition of the test sample plus 1 nM GnRH in 200 $\mu$l 0.1% BSA/McCoy's 5A medium in triplicate wells. Each sample is assayed at 5-dose levels to generate a dose-response curve for determination of its potency on the inhibition of GnRH stimulated LH and/or FSH release. After 4-hr incubation at 37° C., the medium is harvested and the level of LH and/or FSH secreted into the medium determined by RIA.

RIA of LH and FSH

For determination of the LH levels, each sample medium is assayed in duplicates and all dilutions are done with RIA buffer (0.01M sodium phosphate buffer/0.15M NaCl/1% BSA/0.01% NaN3, pH 7.5) and the assay kit is obtained from the Nation Hormone and Pituitary Program supported by NIDDK. To a 12×75 mm polyethylene test tube is added 100 $\mu$l of sample medium diluted 1:5 or rLH standard in RIA buffer and 100 $\mu$l of [125I]-labeled rLH (~30,000 cpm) plus 100 $\mu$l of rabbit anti-rLH antibody diluted 1:187,500 and 100 $\mu$l RIA buffer. The mixture is incubated at room temperature over-night. In the next day, 100 $\mu$l of goat anti-rabbit IgG diluted 1:20 and 100 $\mu$l of normal rabbit serum diluted 1:1000 are added and the mixture incubated for another 3 hr at room temperature. The incubated tubes are then centrifuged at 3,000 rpm for 30 min and the supernatant removed by suction. The remaining pellet in the tubes is counted in a gamma-counter. RIA of FSH is done in a similar fashion as the assay for LH with substitution of the LH antibody by the FSH antibody diluted 1:30,000 and the labeled rLH by the labeled rFSH.

Radio-iodination of GnRH Peptide

The GnRH analog is labeled by the chloramine-T method. To 10 $\mu$g of peptide in 20 $\mu$l of 0.5M sodium phosphate buffer, pH 7.6, is added 1 mCi of Na125I, followed by 22.5

μg chloramine-T and the mixture vortexed for 20 sec. The reaction is stopped by the addition of 60 μg sodium metabisulfite and the free iodine is removed by passing the iodinated mixture through a C-8 Sep-Pak cartridge (Millipore Corp., Milford, Mass.). The peptide is eluted with a small volume of 80% acetonitrile/water. The recovered labeled peptide is further purified by reverse phase HPLC on a Vydac C-18 analytical column (The Separations Group, Hesperia, Calif.) on a Beckman 334 gradient HPLC system using a gradient of acetonitrile in 0.1% TFA. The purified radioactive peptide is stored in 0.1% BSA/20% acetonitrile/0.1% TFA at −800C. and can be used for up to 4 weeks.

GnRH Receptor Membrane Binding Assay

Cells stably, or transiently, transfected with GnRH receptor expression vectors are harvested, resuspended in 5% sucrose and homogenized using a polytron homogenizer (2×15 sec). Nucleii are removed by centrifugation (3000×g for 5 min.), and the supernatant centrifuged (20,000×g for 30 min, 4° C.) to collect the membrane fraction. The final membrane preparation is resuspended in binding buffer (10M Hepes (pH 7.5), 150 mM NaCl, and 0.1% BSA) and stored at −70° C. Binding reactions are performed in a Millipore MultiScreen 96-well filtration plate assembly with polyethylenimine coated GF/C membranes. The reaction is initiated by adding membranes (40 ug protein in 130 ul binding buffer) to 50 ul of [$^{125}$I]-labeled GnRH peptide (~100,000 cpm), and 20 ul of competitor at varying concentrations. The reaction is terminated after 90 minutes by application of vacuum and washing (2×) with phosphate buffered saline. Bound radioactivity is measured using 96-well scintillation counting (Packard Topcount) or by removing the filters from the plate and direct gamma counting. $K_i$ values are calculated from competition binding data using non-linear least squares regression using the Prism software package (GraphPad Software).

The following examples are provided for purposes of illustration, not limitation.

EXAMPLES

In summary, the following Examples disclose the synthesis of representative compounds of this invention. Such compounds may be evaluated for activity as GnRH receptor antagonists according to the methods set forth above.

Examples 1–20

3-Cyano-6-(3-Ethoxycarbonyl)-4-(2-Fluorobenzyl)-2-(4-Methoxyphenyl)-1-Methylpyrrolo[1,2-A]Pyrimid-7-One

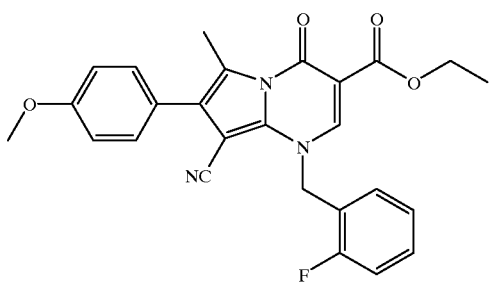

Step A

4'-Methoxy-2-bromopropiophenone

To a flask containing a mixture of CHCl$_3$ (200 mL) and ethyl acetate (200 mL), 4'-methoxypropiophenone (32.8 g, 0.2 mole) was added, followed by addition of copper(II) bromide (89.4 g, 0.4 mole) in several portions. The mixture was then refluxed for 1 hour and stirred at room temperature overnight. The solids were filtered and washed with ethyl acetate (2×100 mL). The filtrated solution was then washed with water (2×100 mL) and dried over Na$_2$SO$_4$. Concentration gave a brown oil which was then dissolved in ether (300 mL) and stored at 0° C. for 1 day. The crystals formed and were filtered and washed with a mixture of ether/hexane (1:1, 2×100 mL), air-dried to give the titled compound (35.5 g, 73%); proton NMR (CDCl$_3$) δ: 8.02 (2H,d, J=9 Hz), 6.95 (2H,d, J=9 Hz). 5.27 (1H,q, J=6.6 Hz), 3.88 (3H, s), 1.89 (3H,d, J=6.6 Hz).

Step B

4'-Methoxy-2-aminopropiophenone hydrochloride

4'-Methoxy-2-bromopropiophenone (10 g, 41 mmol.) was dissolved in a mixture of THF (100 mL) and water (20 mL), followed by addition of sodium azide (6.5 g, 0.1 mole). The slurry was vigorously stirred for 5 hours and TLC indicated a completed conversion to 4'-methoxy-2-azidopropiophenone. The aqueous layer was then removed and the organic layer was further diluted with ethanol (200 mL). Concentrated hydrochloride (5 mL, about 60 mmol.) and palladium on carbon (10%, 2 g) were added and hydrogenation was performed using Parr apparatus at 20 psi for 1 hour. The product precipitated during the hydrogenation was re-dissolved by addition of methanol (100 mL). After filtration to remove the catalyst, the solution was concentrated to form a solid. It was stirred with ether (300 mL) and solids were filtered and dried under vacuum at 50° C. overnight to give the titled compound (8.8 g, 100%) MS: 180 (MH+), 162 (M-NH3). Proton NMR (DMSO-d$_6$) δ: 7.96(2H, brs), 7.79(2H, d, J=8.4 Hz), 6.87(2H, d, J=8.4 Hz), 4.49(1H,brs), 1.17(2H, d, J=6.9 Hz).

Step C

3-Cyano-6-ethoxycarbonyl-2-(4-methoxyphenyl)-1-methyl-4H-pyrrolo[1,2-a]pyrimid-7-one To a refluxing solution (150 mL) of ethanol and water (7/3), NaOH (2.2 g, 55 mmol) and malononitrile (2.64 g, 40 mmol) were added. Then 4'-methoxy-2-aminopropiophenone hydrochloride (5.9 g, 27.2 mmol) was added in several portions. After the solution was refluxed for 30 minutes., additional malonitrile (1.3 g, 20 mmol) and NaOH (1.1 g, 27.5 mmol) were added. It was refluxed for additional 30 minutes and then poured into water (100 mL) which resulted in a precipitation. It was then filtered and washed with water until no color was washed out. The solid was then dried under vacuum at 50° C. overnight to give 2-amino-3-cyano-4-(4-methoxyphenyl)-5-methylpyrrole, (3.9 g, 63%). MS: 228 (MH+).

2-amino-3-cyano-4-(4-methoxyphenyl)-5-methylpyrrole was then refluxed with diethyl ethoxymethylene malonate (2.75 g, 12.7 mmol ) in ethanol for 24 hours and concentrated to a deep brown oil. The oil was mixed with Dowtherm (20 mL) and then heated at 240° C. for 30 minutes. After cooling down to room temperature, it was diluted with ether (200 mL) resulting in a precipitation. The precipitates were filtered, washed with ether (2×100 mL), and air-dried to give the titled compound as a yellow powder (2.8 g, 63%); proton NMR (DMSO-d$_6$) δ: 8.08 (1H, s), 7.09

(2H, d, J=8.1 Hz), 6.84 (2h, d, J=8.1 Hz), 3.97 (2H, q, J=6.9 Hz), 3.57 (3H, s), 2.36 (s, 3H), 1.03 ( 3H,t, J=6.9 Hz); MS: 352 (MH+).

Step D

3-Cyano-6-ethoxycarbonyl-4-(2-fluorobenzyl)-2-(4-methoxyphenyl)-1-methylpyrrolo[1,2-a]pyrimid-7-one To 3-cyano-6-ethoxycarbonyl-2-(4-methoxyphenyl)-1-methyl-4H -pyrrolo[1,2-a]pyrimid-7-one (351 mg, 1.0 mmol.) in dry DMF (5 mL) under $N_2$, 2-fluorobenzyl bromide (473 mg, 2.5 mmol) and silver(I) oxide (924 mg, 4 mmol) were added. The slurry was stirred for 2 days at room temperature and poured into water (10 mL). Crude product was extracted out from water by ethyl acetate (50 mL). The organic layer was then concentrated and purified by silica gel chromatography (ethyl acetate/hexane) to give a pure product. It was crystallized in ether/ethyl acetate to give the titled compound as off white crystals (310 mg, 52%); proton NMR (DMSO-$d_6$): 8.67 (1H, s), 7.45–7.80 (6H, m), 7.00 (2H, d, J=7.8 Hz), 5.70 (2H, s), 4.18 (2H, q, J=6.6 Hz), 3.74 (3H, s), 2.56 (3H, s), 1.23 (3H, t, J=6.6 Hz); MS: 460 (MH+).

By the above procedures, the following compounds were also prepared:

| Example | Ar | $R_4$ | MS (MH+) |
|---|---|---|---|
| 2 | 4-MeO-Ph | cycloPrCH$_2$ | 406 |
| 3 | 4-MeO-Ph | PhCH=CHCH$_2$ | 468 |
| 4 | 4-MeO-Ph | Bn | 442 |
| 5 | 4-MeO-Ph | 2-F-Bn | 460 |
| 6 | 4-MeO-Ph | 2-MeO-Bn | 472 |
| 7 | 4-MeO-Ph | 2-NC-Bn | 467 |
| 8 | 4-MeO-Ph | 2-Cl-Bn | 476 |
| 9 | 4-MeO-Ph | 2,3-F-Bn | 439 |
| 10 | 4-MeO-Ph | 2,4-F-Bn | 439 |
| 11 | 4-MeO-Ph | 2,6-F-Bn | 439 |
| 12 | 4-MeO-Ph | 3,5-F-Bn | 439 |
| 13 | 4-MeO-Ph | 3,5-CF$_3$-Bn | 478 |
| 14 | 4-iBuO-Ph | 2-F-Bn | 502 |
| 15 | 4-iBuO-Ph | 2-MeO-Bn | 514 |
| 16 | 4-iBuO-Ph | 2-NC-Bn | 509 |
| 17 | 4-iBuO-Ph | 2,4-F-Bn | 520 |
| 18 | 4-iBuO-Ph | 2,5-F-Bn | 520 |
| 19 | 4-iBuO-Ph | 2,6-F-Bn | 520 |
| 20 | 4-Br-Ph | 2-F-Bn | 508 |

Examples 21–37

3-Cyano-6-Ethoxycarbonyl-4-(2-Fluorobenzyl)-2-(4-Methoethoxyphenyl)-1-{N-Methyl-N-[2-(2-Pyridyl) Ethyl]Aminomethylpyrrolo[1,2-A]Pyrimid-7-One

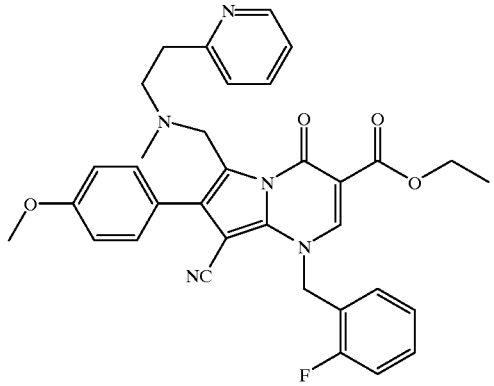

To 3-cyano-6-ethoxycarbonyl-4-(2-fluorophenyl)-2-(4-methoxyphenyl)-1-methylpyrrolo[1,2-a]pyrimidone (460 mg, 1.0 mmol) (from Example 1 above) in refluxing $CCl_4$ (30 mL), NBS (235 mg, 1.4 mmol) and 3 particles of benzoyl peroxide were added. It was refluxed for 30 minutes and cooled down to room temperature. Triethylamine (1 mL) and acetonitrile (2 mL) and 2-(N-methylaminoethyl) pyridine were added. It was then stirred at room temperature for 30 minutes. Concentration gave an oil which was purified by prep-TLC plate ($CHCl_3$/MeOH/$NH_4OH$=200/50/1), producing the titled compound as a pure product (220 mg, 37%). Proton NMR (CDCl$_3$) δ: 8.23 (1H, d, J=4.5 Hz), 8.19 (1H,s), 7.53–7.11 (9H, m), 6.95 (2H, d, J=8.4 Hz), 5.61 (2H, s), 4.34 (2H, q, J=7.2 Hz), 4.17 (2H, brs), 3.84 (3H, s), 2.95–2.75 (4H, m), 2.15 (3H, s), 1.34 (3H, t, J=7.2 Hz); MS: 594 (MH+).

By the above procedures, the following compounds were also prepared:

| Example | $R_1NR_2$ | MS (M + H) |
|---|---|---|
| 22 | BnNMe | 579 |
| 23 | 4-pyridylCH$_2$NMe | 594 |
| 24 | 3,4-Cl-PhCH$_2$NMe | 662 |
| 25 | PropargylNMe | 527 |
| 26 | CydoPrCH$_2$NPr | 571 |
| 27 | MeNMe | 503 |
| 28 | 3-pyridyl(CH$_2$)$_4$NMe | 622 |
| 29 | 2-pyridyl(CH$_2$)$_2$NMe | 594 |
| 30 | 6-Me-2-pyridylCH$_2$NMe | 594 |
| 31 | 2-fururylCH$_2$NMe | 569 |

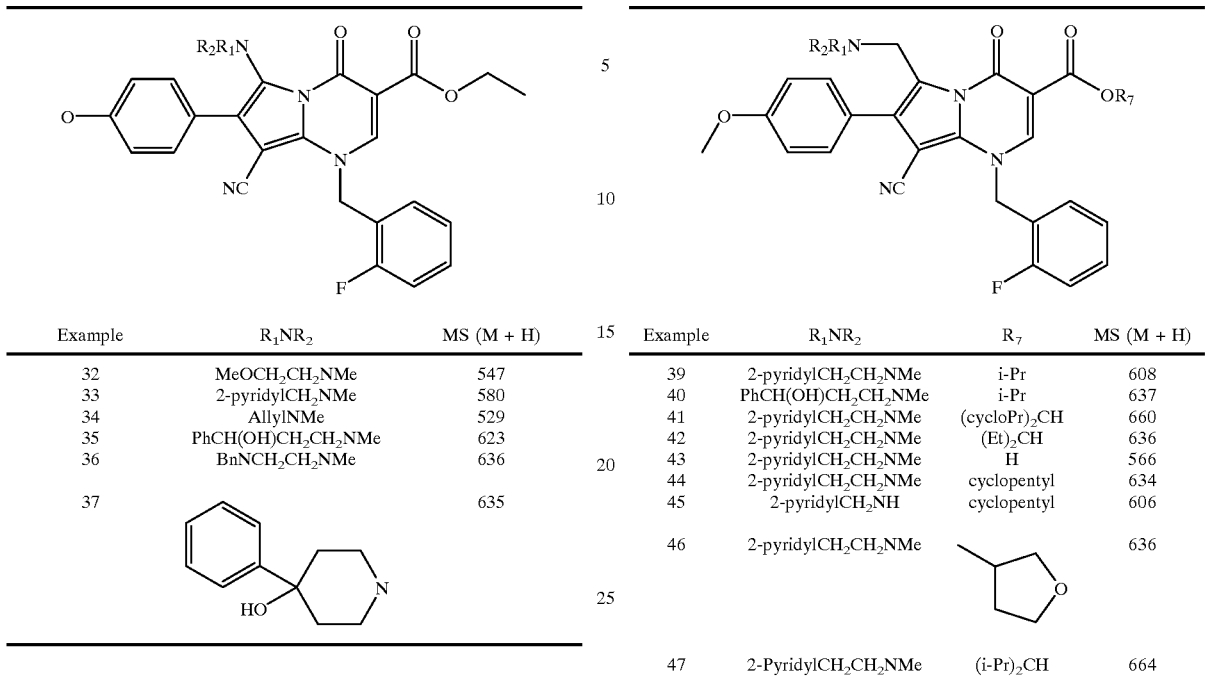

| Example | R₁NR₂ | MS (M + H) |
|---|---|---|
| 32 | MeOCH₂CH₂NMe | 547 |
| 33 | 2-pyridylCH₂NMe | 580 |
| 34 | AllylNMe | 529 |
| 35 | PhCH(OH)CH₂CH₂NMe | 623 |
| 36 | BnNCH₂CH₂NMe | 636 |
| 37 | 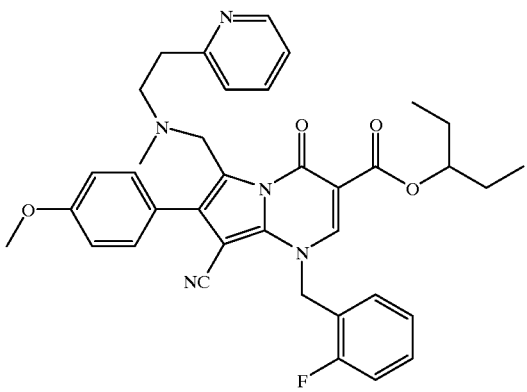 | 635 |

Examples 38–47

3-Cyano-6-(3-Pentyloxycarbonyl)-4-(2-Fluorobenzyl)-2-(4-Methoxyphenyl)- 1-{N-Methyl-N-[2-(2-Pyridyl)Ethyl]Aminomethylpyrrolo[1,2-A]Pyrimid-7-One

38

To 3-cyano-6-ethoxycarbonyl-4-(2-fluorophenyl)-2-(4-methoxyphenyl)-1-{N-methyl-N-[2-(2-pyridyl)ethyl]aminomethylpyrrolo[1,2-a]pyrimidone (59 mg, 0.1 mmol) in dry THF (2 mL) under nitrogen atmosphere was added 3-pentanol (0.5 mL) and KN(TMS)₂ in toluene (0.5M, 3 mL, 1.5 mmol). The mixture was stirred for 30 minutes, quenched by ethyl acetate (30 mL) and HCl (2N, 10 mL). The organic layer was separated, concentrated and purified by Prep-TLC to give the titled compound (18 mg, yield 28%). Proton NMR (CDCl₃) δ: 8.43 (1H, d, J=5.1 Hz), 8.16 (1H, s), 7.54–6.96 (9H, m), 6.98 (2H, d, J=8.7 Hz), 5.62 (2H, s), 5.00–4.92 (1H, m), 4.12 (2H, s), 3.87 (3H, s), 2.90–2.80 (2H, m), 2.80–2.70 (2H, m), 2.11 (3H, s), 1.70–1.61 (4H, m), 0.92 (6H, t, J=7.2 Hz); MS: 636 (MH+)

By the above procedure, the following compounds were also prepared:

| Example | R₁NR₂ | R₇ | MS (M + H) |
|---|---|---|---|
| 39 | 2-pyridylCH₂CH₂NMe | i-Pr | 608 |
| 40 | PhCH(OH)CH₂CH₂NMe | i-Pr | 637 |
| 41 | 2-pyridylCH₂CH₂NMe | (cycloPr)₂CH | 660 |
| 42 | 2-pyridylCH₂CH₂NMe | (Et)₂CH | 636 |
| 43 | 2-pyridylCH₂CH₂NMe | H | 566 |
| 44 | 2-pyridylCH₂CH₂NMe | cyclopentyl | 634 |
| 45 | 2-pyridylCH₂NH | cyclopentyl | 606 |
| 46 | 2-pyridylCH₂CH₂NMe | (tetrahydrofuranyl) | 636 |
| 47 | 2-PyridylCH₂CH₂NMe | (i-Pr)₂CH | 664 |

Examples 48–63

The following compounds were made by the procedures set forth in the preceding Examples.

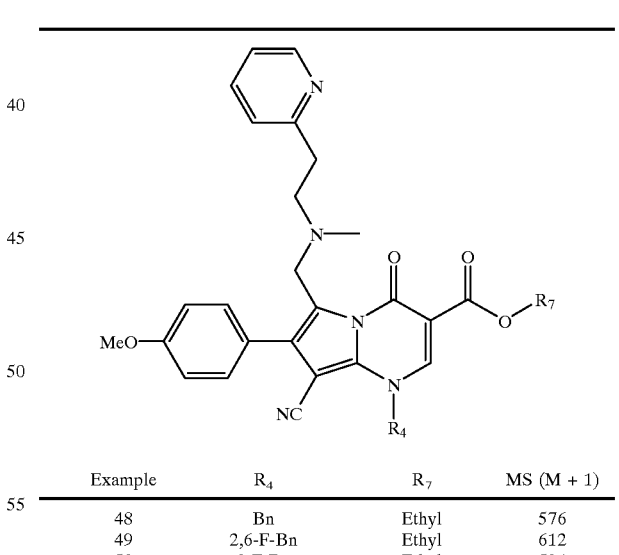

| Example | R₄ | R₇ | MS (M + 1) |
|---|---|---|---|
| 48 | Bn | Ethyl | 576 |
| 49 | 2,6-F-Bn | Ethyl | 612 |
| 50 | 2-F-Bn | Ethyl | 594 |
| 51 | PhCH=CHCH₂ | Ethyl | 602 |
| 52 | CycloPrCH₂ | Ethyl | 540 |
| 53 | 2-Cl-Bn | Ethyl | 610 |
| 54 | 3,5-CF₃-Bn | Ethyl | 712 |
| 55 | 2-MeO-Bn | Ethyl | 606 |
| 56 | 2-MeO-Bn | i-Pr | 620 |
| 57 | 2-MeO-Bn | 3-pentyl | 648 |
| 58 | 3,5-F-Bn | Ethyl | 612 |
| 59 | 2-F-Bn | (cycloPr)₂CH | 660 |
| 60 | 2-NC-Bn | Ethyl | 601 |
| 61 | 2-F-Bn | H | 566 |

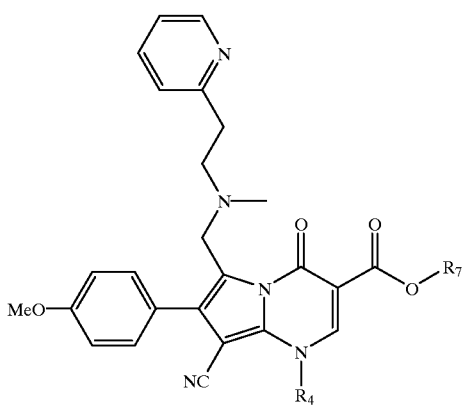

| Example | R$_4$ | R$_7$ | MS (M + 1) |
|---|---|---|---|
| 62 | 2,4-F-Bn | Ethyl | 612 |
| 63 | 23-F-Bn | Ethyl | 612 |

Example 64

3-Cyano-6-(3-pentyloxycarbonyl)-4-(2-fluorobenzyl)-2-[4-(3-pentyl)oxyphenyl]-1-{N-methyl-N-[2-(2-pyridyl)ethyl]aminomethylpyrrolo[1,2-a]pyrimid-7-one

64

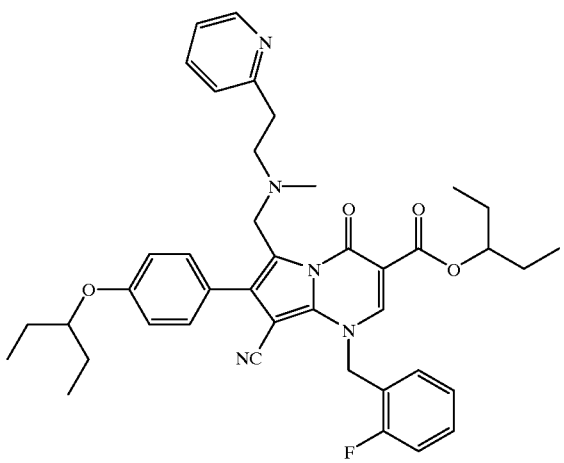

Step A

3-Cyano-6-(3-hydroxycarbonyl)-4-(2-fluorobenzyl)-2-(4-hydroxyphenyl)-1-{N-methyl-N-[2-(2-pyridyl)ethyl]aminomethylpyrrolo[1,2-a]pyrimid-7-one To a stirred solution of 3-cyano-6-(3-ethoxycarbonyl)-4-(2-fluorobenzyl)-2-(4-methoxyphenyl)-1-methylpyrrolo[1,2-a]pyrimid-7-one (230 mg, 0.5 mmol) in dry DCM (2 mL) at −78° C. under atmosphere of N$_2$, Boron tribromide (4 mL, 1M in DCM) was added dropwise. After completion of the addition, the cooling bath was removed and the mixture was warmed to room temperature and stirred for 5 hours. It was then poured into stirring water (10 mL) resulting in a precipitation. The precipitates were filtered, washed with water (2×20 mL), ether (10 mL), dried to give the titled product (150 mg, 72%). MS: 418 MH$^+$), 400 (M-OH)$^+$.

Step B

3-Cyano-6-(3-pentoxycarbonyl)-4-(2-fluorobenzyl)-2-[4-(3 -pentoxyphenyl]-1-methylpyrrolo[1,2-a]pyrimid-7-one To a stirred solution of 3-Cyano-6-(3-hydroxycarbonyl)-4-(2-fluorobenzyl)-2-(4-hydroxyphenyl)-1-methylpyrrolo[1,2-a]pyrimid-7-one (83 mg, 0.2 mmol) in dry DMF (5 mL) under atmosphere of N$_2$, potassium carbonate (500 mg, 3.6 mmol.) was added, followed by addition of 3-bromopentane (0.5 mL, 4.0 mmol.). The slurry was heated at 90° C. overnight and treated with ethyl acetate (20 mL) and water (20 mL). The organic layer was separated and filtered through a silica gel pad (10 g), washed with ethyl acetate. It was then concentrated to give the titled product, essentially pure by TLC (85 mg, 76%). MS: 558 (MH$^+$).

Step C

3-Cyano-6-(3-pentoxycarbonyl)-4-(2-fluorobenzyl)-2-[4-(3-pentoxy)phenyl]-1-{N-methyl-N-[2-(2-pyridyl)ethyl]aminomethylpyrrolo[1,2-a]pyrimid-7-one To a refluxing solution of carbon tetrachloride (5 mL) containing 3-cyano-6-(3-pentoxycarbonyl)-4-(2-fluorobenzyl)-2-[4-(3-pentoxyphenyl]-1-methylpyrrolo[1,2-a]pyrimid-7-one (85 mg, 0.15 mmol), NBS (43 mg, 1.5 eq) and 3 particles of benzoyl peroxide were added in one portion. It was refluxed for 1 hour to give the bromo compound. The solution was then divided into 4 portion equally. To one portion with stirring, 1 drop of 2-(N-methylethyl)pyridine was added. After stirred for 5 minutes, it was purified by prep-TLC plate (CHCl$_3$/MEOH/NH$_4$OH= 500/50/1) to give the pure titled product as an oil (9.0 mg, 35%). NMR (CDCl$_3$, δ): 8.42 (1H, d, J=3.9 Hz), 8.14 (1H, s), 7.52–6.92 (11H, m), 5.60 (2H, s), 4.96–4.89 (1H, m), 4.16–4.11 (2H, m), 2.90–2.70 (4H, ,m), 2.13 (3H, s), 1.75–1.59 (8H, m), 1.00–0.87 (12H, m). MS: 678 (MH$^+$).

Examples 65–75

2-(2,5-dimethyl-3-furyl)-3-{N-methyl-N-[2-(2-pyridyl)ethyl]aminomethyl}-5-(3-methoxyphenyl)-6-methyl-7-(2-fluorophenylmethyl)imidazolo[1,2-a]-pyrimid-4-one

65

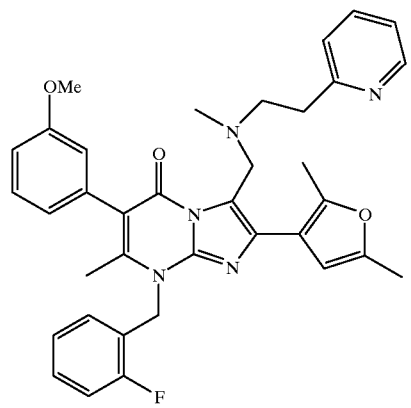

Step A 3-(Bromoacetyl)-2,5-dimethylfuran

Copper bromide (17.9 g, 2.0 eq) was added to a solution of the 2,5-dimethyl 3-acetofuran (5.52 g, 40 mmol) in EtOAc/CHCl3 (1:1, 50 mL). The mixture was refluxed for 2.5 hours, at which time the starting material was almost totally consumed. It was then cooled down and filtered to remove the copper residue. The green filtrate was concentrated to yield an oil which was diluted with ether, filtered again to further remove some black insoluble residue. The filtrate was then concentrated to yield an oil (6.5 g) as the desired product, which was directly used in the next step.

Step B 2-(2,5-dimethyl-3-furyl)-5-bromo-6-methylimidazolo[1,2-a]pyrimid-4-one 2-amino-5-bromo-6-methylpyrimidin-4-ol (2.04 g, 10 mmol) suspended in DMF was treated with NaH (60%, 520 mg, 1.3 eq) carefully. A lot of bubbles were generated. The mixture was stirred at room temperature for 30 minutes. 3-(Bromoacetyl)-2,5-dimethylfuran dissolved in DMF was added dropwise. The brown solution was stirred at room temperature for 3 hours. It was then dumped into iced 1N HCl. Precipitate generated was filtered and washed with water, ether and dried to yield a solid as the desired product (2.8 g); MS m/e 324 (M+H).

Step C 2-(2,5-Dimethyl-3-furyl)-5-bromo-6-methyl-7-(2-fluorophenylmethyl)imidazolo[1,2-a]pyrimid-4-one 2-(2,5-Dimethyl-3-furyl)-6-methylimidazolo[1,2-a]pyrimid-4-one (1 g, 3.1 mmol) was suspended in DME (6 mL), treated with TBAF (1M in THF, 4.65 mL, 1.5 eq) to yield a clear solution, 2-fluorobenzyl bromide was then added. The mixture was stirred at room temperature for 3 hours, the precipitate generated was filtered and washed with water (50 mL), ehter (50 mL) to yield a white solid (203 mg); MS: m/e 430 (M+H).

Step D 2-(2,5-Dimethyl-3-furyl)-5-(3-methoxyphenyl)-6-methyl-7-(2-fluorophenylmethyl)imidazolo[1,2-a]pyrimid-4-one 2-(2,5-Dimethyl-3-furyl)-5-bromo-6-methyl-7-(2-fluorophenylmethyl)-imidazolo[1,2-a]pyrimid-4-one (200 mg, 0.466 mmol), boronic acid (74 mg, 1.05 eq.), Pd(OAc)$_2$ (5.2 mg, 0.05 eq), PPh$_3$ (12 mg, 0.1 eq), K$_2$CO$_3$ (129 mg, 2.0 eq) were the reaction flack, degassed and protected under N$_2$ atmosphere. Toluene (4 mL) and H$_2$O (1 mL) were then added. The mixture was refluxed at 110° C. for 6 hours. MS indicated about ¼of the bromide was still remained unchanged. The reaction was stopped by filtering off the Pd catalyst. The filtrate was partitioned between EtOAc and water. The organic layer was concentrated to yield a light yellow solid as the crude product which was directly used in the next step without further purification (200 mg); MS: m/e 458 (M+H).

Step E 2-(2,5-dimethyl-3-furyl)-3-{N-methyl-N-[2-(2-pyridyl)ethyl]aminomethyl}-5-(3-methoxyphenyl)-6-methyl-7-(2-fluorophenylmethyl)imidazolo[1,2-a]pyrimid-4-one 2-(2,5-Dimethyl-3-furyl)-5-(3 -methoxyphenyl)-6-methyl-7-(2-fluorophenylmethyl)imidazolo[1,2-a]pyrimid-4-one (30 mg) obtained above as suspended in acetic acid and treated with 2 drops of amine followed by 2 drops of the formaldehyde (37% water solution). The reaction was stirred at room temperature for 1 hour. HOAc was evaporated and the residue was diluted with DCM and purified by prep-TLC to yield the desired product, which was characterized by proton NMR and mass spectra.

Following procedures similar to that described above, the compounds listed below were also prepared.

| Ex. | —C(R$_{3a}$R$_{3b}$)$_m$NR$_1$R$_2$ | MS (M + H) | Proton NMR |
|---|---|---|---|
| 65 | —CH$_2$N(Me)(CH$_2$CH$_2$-2-Py) | 606 | 2.24(s, 3H), 2.27(s, 3H), 2.97(m, 4H), 3.80(s, 3H), 4.11(s, 2H), 5.62 (s, 2H), 6.08(s, 1H), 6.80–7.58(m, 11H), 8.41(m, 1H) |
| 66 | —CH$_2$N(Me)(Bn) | 591 | 2.18(s, 3H), 3.24(s, 3H), 3.40(s, 3H), 3.61(s, 2H), 3.82(s, 2H), 4.13 (s, 2H), 5.64(s, 2H), 6.31(s, 1H), 6.80–7.39(m, 13H) |
| 67 | —CH$_2$N(Me)(CH$_2$NEt$_2$) | 600 | |
| 68 | —CH$_2$N(Me)(CH$_2$CH$_2$OMe) | 559 | |

-continued

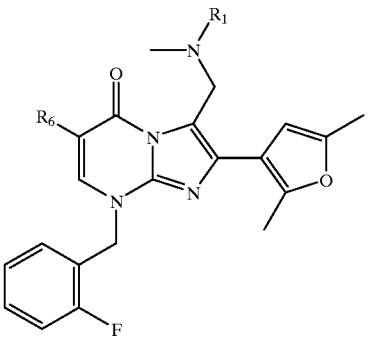

| Ex. | R₁ | R₆ | MS (M + H) |
|---|---|---|---|
| 69 | —Bn | 3-EtOPh | 605 |
| 70 | —CH₂CH₂-2-Py | 3-EtOPh | 620 |
| 71 | —Bn | 3-FPh | 579 |
| 72 | —CH₂CH₂-2-Py | 3-FPh | 594 |
| 73 | —Bn | 3-Py | 562 |
| 74 | —CH₂CH₂-2-Py | 3-Py | 577 |
| 75 | —CH₂CH₂NMe₂ | 3-Py | 543 |

Examples 76–77

2-(2,5-dimethyl-3-furyl)-1-{N-methyl-N-[2-(2-pyridyl)ethyl]aminomethyl}-6-ethoxycarbonyl-4-(2-fluorophenylmethyl)pyrrolo[1,2-a]pyrimid-7-one

76

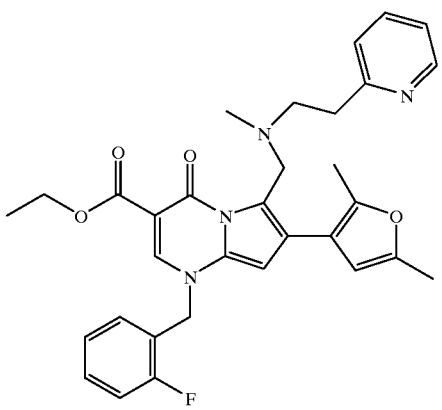

Step A

1-[2-(2,5-Dimethyl-3-furyl)-2-oxoethyl]-2-methyl-5-ethoxycarbonylpyrimid-6-one

5-Ethoxycarbonyl-2-methylpyrimid-4-one (3.5 g, 19 mmol) was dissolved in DME (110 mL) and TBAF (28.5 mL, 1 M solution in THF, 28.5 mmol) added dropwise at 0° C. The resulting solution was stirred ten minutes and a solution of 3-bromoacetyl-2,5-dimethylfuran (4.3 g, 20 mmol) in DME (10 mL) was added dropwise. The reaction was stirred at room temperature overnight. The solution was then concentrated in vacuo and partitioned between EtOAc and saturated aqueous NH₄Cl. The EtOAc layer was separated and concentrated. The product was purified using flash silica chromatography (EtOAc/hexane=2:8 to 8:2), with the o-alkylated side product eluting at 4:6, and the desired N-alkylated product eluting at 8:2. The N-alkylated product was dried as a yellow solid, isolated in 31% yield; MS: 319 (M+H) and 273.

Step B 2-(2,5-Dimethyl-3-furyl)-4H-6-ethoxycarbonylpyrrolo[1,2-a]pyrimid-7-one

1-[2-(2,5-Dimethyl-3-furyl)-2-oxoethyl]-2-methyl-5-ethoxycarbonyl-pyrimid-6-one (1.94 g, 6.1 mmol) was dissolved in EtOH and added dropwise to a NaOEt solution, prepared in situ by dissolving sodium (280 mg) in dry EtOH (70 mL) under N₂. The mixture was stirred at room temperature for one hour, concentrated and acidified with 6N HCl to pH=5. This resulted in a yellow-orange solid, which was collected by filtration and dried to give the product as a medium brown solid; MS: 301 (M+H)) and 255.

Step C 2-(2,5-Dimethyl-3-furyl)-6-ethoxycarbonyl-4-(2-fluorophenylmethyl)pyrrolo[1,2-a]pyrimid-7-one 2-(2,5-Dimethyl-3-furyl)-4H-6-ethoxycarbonylpyrrolo[1,2-a]pyrimid-7-one (1.83 g, 6.1 mmol) was suspended in DME (10 mL), followed by addition of TBAF (12.2 mL, 1M solution in THF, 12.2 mmol), and then 2-fluorobenzyl bromide. The solution was stirred at room temperature overnight. A solid precipitate was collected by filtration and washed with Et₂O to yield the product; MS: 409 (M+H) and 363.

Step D 2-(2,5-Dimethyl-3-furyl)-1-{N-methyl-N-[2-(2-pyridyl)ethyl]aminomethyl}-6-ethoxycarbonyl-4-(2-fluorophenylmethyl)pyrrolo[1,2-a]pyrimid-7-one 2-(2,5-Dimethyl-3-furyl)-6-ethoxycarbonyl-4-(2-fluorophenylmethyl)-pyrrolo[1,2-a]pyrimid-7-one (50 mg, 122 umol) was added into a solution of formaldehyde (5 μL, 184 μmol) and a secondary amine (184 μmol) in acetic acid (2 mL). The resulting solution was stirred at room temperature for ten minutes, and then 50° C. for another ten minutes. HOAc was evaporated and the residue was diluted with DCM and purified by prep-TLC (MeOH/DCM–1:9) to yield the desired product, which was characterized by proton NMR and mass spectra.

Following the above procedures, the following compounds were prepared.

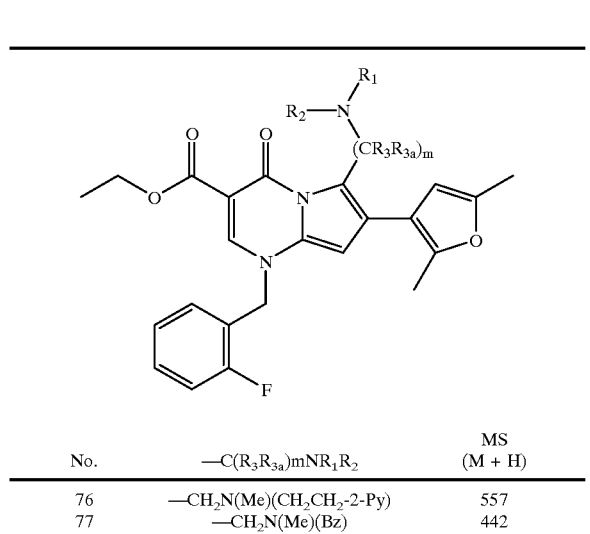

| No. | —C(R₃R₃ₐ)mNR₁R₂ | MS (M + H) |
|---|---|---|
| 76 | —CH₂N(Me)(CH₂CH₂-2-Py) | 557 |
| 77 | —CH₂N(Me)(Bz) | 442 |

Examples 78–84

1-{N-methyl-N-[2-(2-pyridyl)ethyl]aminomethyl-3-fluoro-4-(2-fluorobenzyl)-2-[4-(2-methylpropyloxy)phenyl]-6-(ethyloxycarbonyl)pyrrolo[1,2-a]pyrimid-7-one

78

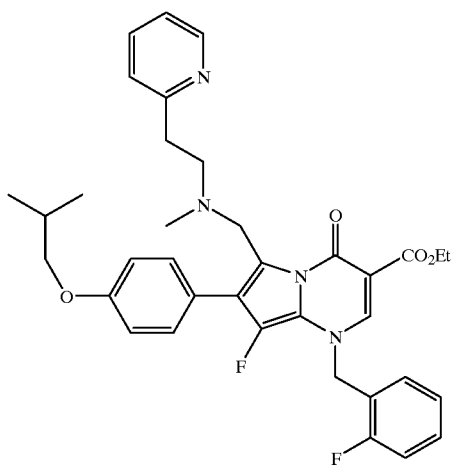

Step A
Fluoroacetamidine

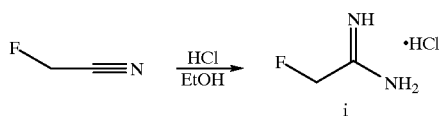

HCl gas was bubbled into fluoroacetonitrile (11 g, 186 mmol) at 0–20° C. until the reaction mixture solidified. Precooled EtOH (40 mL) was added to solid at –50° C. and the reaction was allowed to warm to room temperature overnight. Ether (200 mL) was added and the solid product i was filtered and washed with ether to give a total of 15.72 g of white solid (yield=75%).

Step B
Ethyl-(2-fluoromethylpyrimid-4-one)-5-carboxylate

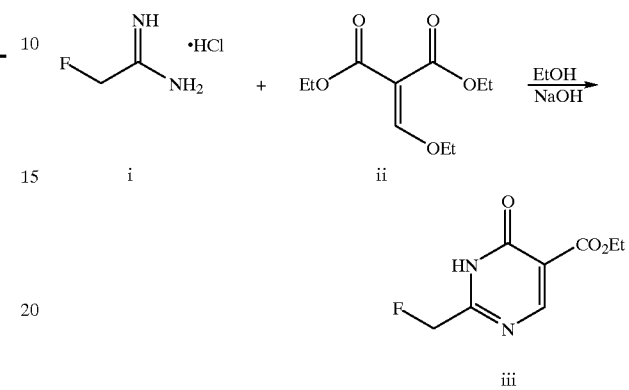

Sodium hydroxide (4.0 g, 100 mmol) was added to a mixture of amidine i (5.63 g, 50 mmol) and ester ii (11.1 mL, 55 mmol) in EtOH (250 mL). The suspension was heated at reflux for 7 hr. After cooling to room temperature, the mixture was poured into water and acidified with a 10% HCl solution. Extraction with EtOAc followed by evaporation and trituration with ether gave pyrimidone iii as a solid (2.59 g, 26% yield).

Step C
4'-(2-methylpropyloxy)acetophenone

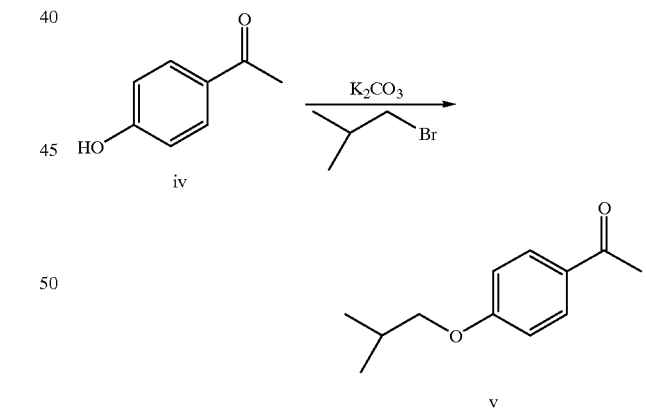

4'-Hydroxyacetophenone iv (6.81 g, 50 mmol) was dissolved in EtOH (170 mL). Potassium carbonate (13.8 g, 100 mmol) and 1-bromo-2-methylpropane (6 mL, 55 mmol) were added and the reaction refluxed for 50 hr. Water (500 mL) was added followed by extraction with EtOAc. Evaporation of the organic layer after washes with 1M sodium hydroxide and brine gave v as an amber oil (3.95 g, 41% yield).

Step D
2-Bromo-4'-(2-methylpropyloxy)acetophenone

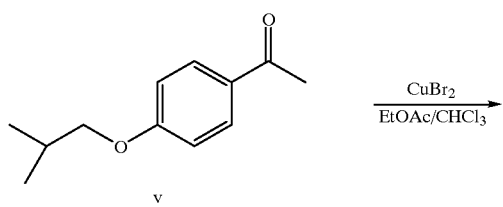

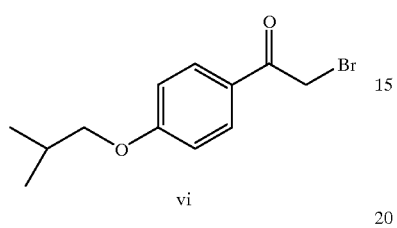

Acetophenone v (3.5 g, 18.2 mmol) and CuBr$_2$ (8.14 g, 36.5 mmol) in chloroform/EtOAc (1;1, 35 mL) were heated at reflux for 2 hr. After filtration, the organic layer was washed, dried, filtered, and evaporated to give alpha-bromoketone vi (4.4 g, 89% yield).

Step E
Ethyl-2-fluoroethyl-3-[4-(2-methylpropyloxy)phenyl]carbonylmethyl-6-(ethyloxycarbonyl)pyrimid-4-one-5-carboxylate

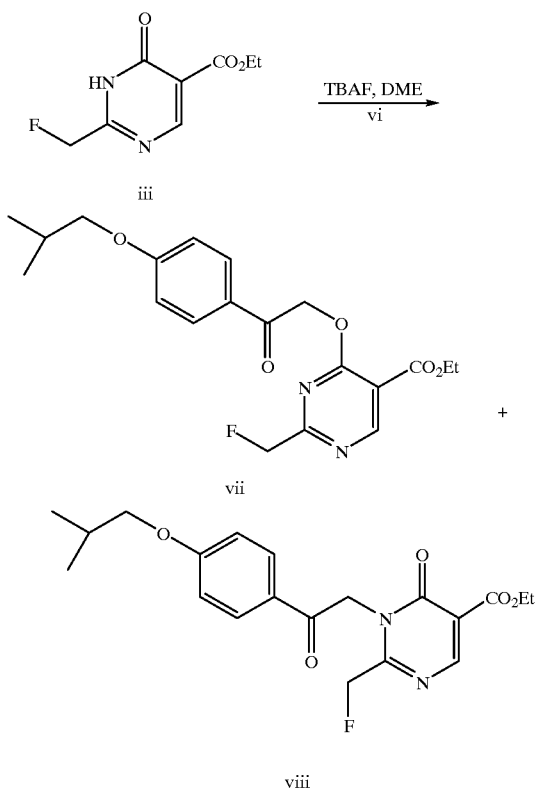

Tetrabutylammonium fluoride in THF (9.0 mL, 1.0M) was added to a suspension of iii (1.0 g, 5 mmol) in dimethoxyethane (30 mL). After 30 min, bromoketone vi (1.49 g, 5.5 mmol) in DME (2 mL) was added and the reaction mixture was stirred at room temperature overnight. Column chromatography using hexane/ethyl acetate as elut-ant gave isomer vii (794 mg, 41% yield) and product viii (434 mg, 22%).

Step F
3-Fluoro-2-[4-(2-methylpropyloxy)phenyl]-6-(ethyloxycarbonyl)pyrrolo[1,2-a]pyrimid-7-one

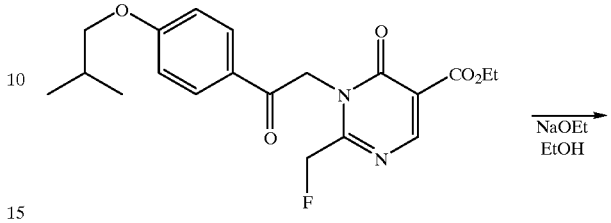

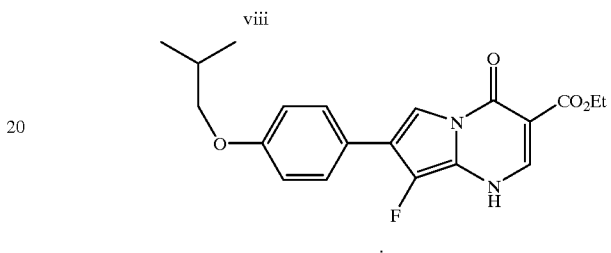

Pyrimidone ester viii (430 mg, 1.1 mmol) was added to a solution of sodium ethoxide (63 mg Na in 14 mL EtOH) and the reaction mixture was stirred at room temperature for 4 hr. Acidification of the reaction mixture with 10% HCl resulted in a fine precipitate which was filtered and combined with an EtOAc wash resulting in solid ix (410 mg, 99% yield).

Step G
3-Fluoro-4-(2-fluorobenzyl)-2-[4-(2-methylpropyloxy)phenyl]-6-(ethyloxycarbonyl)pyrrolo[1,2-a]pyrimid-7-one

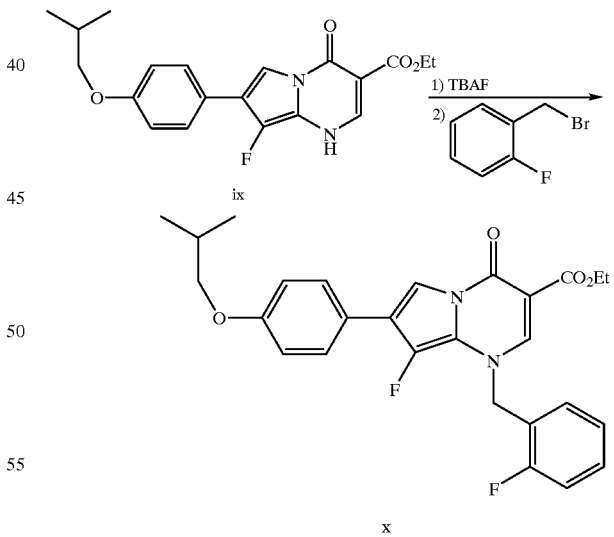

A solution of 1.0 M tetrabutylammonium fluoride in THF (1.21 mL) was added to a suspension of ix (410 mg, 1.1 mmol) in DME (8 mL). The resulting solution was stirred for 30 minutes. 2-Fluorobenzylbromide (0.16 mL, 1.3 mmol) was added and the reaction mixture was stirred for 19 hours. Workup involving extraction with EtOAc, aqueous wash of the EtOAc layer, and chromatography with EtOAc/hexane gave x (116 mg, 22%).

Step H
1-{N-Methyl-N-[2-(2-pyridyl)ethyl]aminomethyl-3-fluoro-4-(2-fluorobenzyl)-2-[4-(2-methylpropyloxy)phenyl]-6-(ethyloxycarbonyl)pyrrolo[1,2-a]pyrimid-7-one

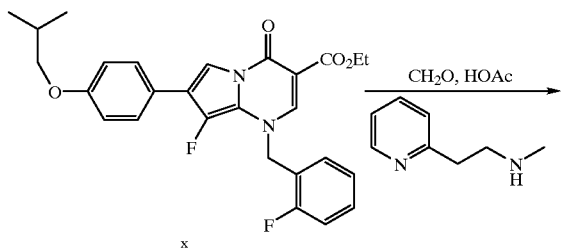

x

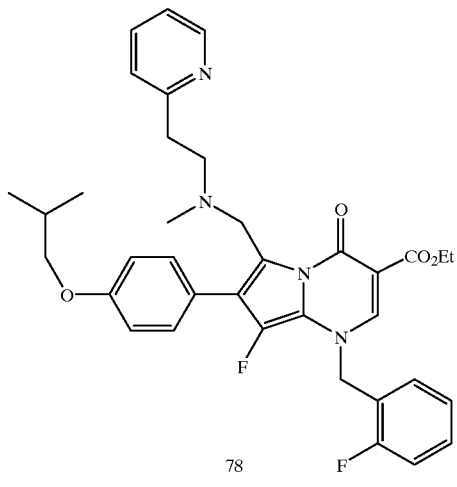

78

Pyrrolopyrimidone ester x (30 mg, 0.0625 mmol) was added to glacial acetic acid (1 mL), formaldehyde (2 drops), and 2-(2-methylaminoethyl)pyridine (2 drops). After 1 hour, extraction with EtOAc, purification by prep TLC using CHCl$_3$/MeOH/NH$_4$OH, and trituration with ether gave the titled product, 71, as a white solid (10 mg, 26%).

Following procedures similar to that described above, the compounds listed below were also prepared.

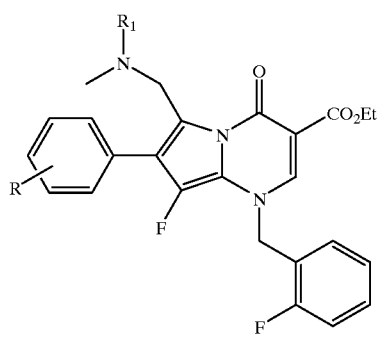

| Ex. | R | R$_1$ | MS (M + H) |
|---|---|---|---|
| 79 | 4-(CH$_3$)$_2$CHCH$_2$O— | (2-Pyridyl)CH$_2$CH$_2$— | 629 |
| 80 | 4-(CH$_3$)$_2$CHCH$_2$O— | Bn | 614 |
| 81 | 4-(CH$_3$)$_2$CHCH$_2$O— | (2-Furyl)CH$_2$— | 604 |
| 82 | 3-CH$_3$O— | Bn | 572 |

-continued

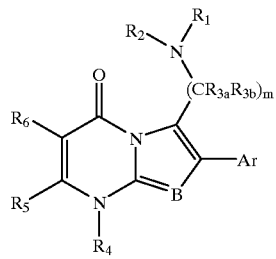

| Ex. | R | R$_1$ | MS (M + H) |
|---|---|---|---|
| 83 | 3-CH$_3$O— | (2-Furyl)CH$_2$— | 562 |
| 84 | 3-CH$_3$O— | (2-Pyridyl)CH$_2$CH$_2$— | 587 |

It will be appreciated that, although specific embodiments of the invention have been described herein for purposes of illustration, various modifications may be made without departing from the spirit and scope of the invention. Accordingly, the invention is not limited except as by the appended claims.

We claim:

1. A compound having the following structure:

and stereoisomers, prodrugs and pharmaceutically acceptable salts thereof, wherein:

m is an integer from 1 to 6;

R$_1$ is hydrogen, alkyl, substituted alkyl, aryl, substituted aryl, arylalkyl, substituted arylalkyl, heteroaryl, substituted heteroaryl, heteroarylalkyl, substituted heteroarylalkyl, aryl(CR$_{3c}$R$_{3d}$)$_n$, substituted aryl (CR$_{3c}$R$_{3d}$)$_n$, heteroaryl(CR$_{3c}$R$_{3d}$)$_n$ or substituted heteroaryl(CR$_{3c}$R$_{3d}$)$_n$;

R$_2$ is hydrogen, alkyl or substituted alkyl;

or R$_1$ and R$_2$ taken together with the nitrogen atom to which they are attached form a heterocycle ring or a substituted heterocycle ring;

R$_{3a}$, R$_{3b}$, R$_{3c}$ and R$_{3d}$ are the same or different and independently at each occurrence hydrogen, alkyl, substituted alkyl, hydroxy, alkoxy, thioalkyl, amino, alkylamino, dialkylamino, cyano, halogen, —C(=O) OR$_7$ or —C(=O)NR$_7$R$_8$;

or R$_{3a}$ and R$_{3b}$, or R$_{3c}$ and R$_{3d}$, taken together with the carbon atom to which they are attached form a carbocyclic ring or substituted carbocyclic ring;

or R$_{3a}$ and R$_1$, taken together with the carbon atom and nitrogen atom, respectively, to which they are attached form a heterocyclic ring or substituted heterocyclic ring;

$R_4$ is hydrogen, alkyl, substituted alkyl, aryl, substituted aryl, arylalkyl, substituted arylalkyl, heteroaryl, substituted heteroaryl, heteroarylalkyl or substituted heteroarylalkyl;

$R_5$ is hydrogen, halogen, cyano, alkyl, substituted alkyl, hydroxy, alkoxy, thioalkyl or mono- or di-alkylamine;

$R_6$ is hydrogen, alkyl, substituted alkyl, aryl, substituted aryl, heterocycle, substituted heterocycle, —$OR_7$, —$SR_7$, —$SOR_7$, —$SO_2R_7$, —$OSO_2R_7$, —$SO_2OR_7$, —$SO_2NR_7R_8$, —$NR_9SO_2R_7$, —$C(=O)R_7$, —$C(=O)OR_7$, —$OC(=O)R_7$, —$NR_7R_8$, —$C(=O)NR_7R_8$, —$OC(=O)NR_7R_8$, —$NR_9C(=O)R_7$, —$NR_9C(=O)NR_7R_8$, —$NR_8C(=O)OR_7$ or —$C(OH)R_7R_8$;

$R_7$, $R_8$ and $R_9$ are the same or different and independently hydrogen, alkyl, substituted alkyl, aryl, substituted aryl, arylalkyl, substituted arylalkyl, heteroaryl, substituted heteroaryl, heteroarylalkyl or substituted heteroarylalkyl;

or $R_7$ and $R_8$ taken together with the nitrogen atom to which they are attached form a heterocycle ring or a substituted heterocycle ring;

n is an integer from 1 to 6; and

B and Ar are as follows:
B is nitrogen or $CR_{10}$ when Ar is heteroaryl or substituted heteroaryl and $R_{10}$ is hydrogen; or
B is $CR_{10}$ when Ar is aryl, substituted aryl, heteroaryl or substituted heteroaryl and $R_{10}$ is halogen, cyano, nitro, amino, mono- or di-alkylamino or alkyl.

2. The compound of claim 1 wherein
B is nitrogen or $CR_{10}$;
$R_{10}$ is hydrogen; and
Ar is heteroaryl or substituted heteroaryl.

3. The compound of claim 1 wherein
B is $CR_{10}$;
$R_{10}$ is halogen, cyano, nitro, amino, mono- or di-alkylamino or alkyl; and
Ar is aryl, substituted aryl, heteroaryl or substituted heteroaryl.

4. The compound of claim 2 wherein B is nitrogen and Ar is heteroaryl.

5. The compound of claim 4 having the following structure:

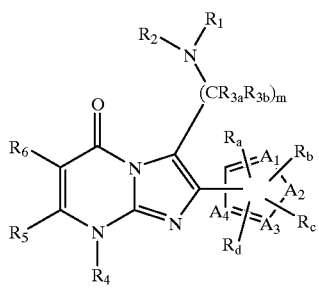

wherein
$A_1$, $A_3$ and $A_4$ are the same or different and independently nitrogen or CH;
$A_2$ is oxygen, sulfur, NH, N=N or N=CH; and
$R_a$, $R_b$, $R_c$, and $R_d$ are optional substituents that are the same or different and independently halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, hydroxy, alkoxy, aryloxy, thiol, thioalkyl, thioaryl, sulfonylalkyl, sulfonylaryl, amino, mono- or di-alkylamino, mono- or di-arylamino, —COOalkyl, —COOaryl, —CONHalkyl, —CONHaryl, —CON(alkyl)$_2$, —CON(aryl)$_2$, —NHCOalkyl, —NHCOaryl, —N(alkyl)COalkyl, —N(alkyl)COaryl, —NHSO$_2$alkyl, —NHSO$_2$aryl, N(alkyl)SO$_2$alkyl, —N(alkyl)SO$_2$aryl, —NHCONHalkyl or —NHCONHaryl;

or $R_a$ and $R_b$ taken together with the atoms to which they are attached form aryl, substituted aryl, heteroaryl or substituted heteroaryl.

6. The compound of claim 2 wherein B is $CR_{10}$, Ar is heteroaryl, and $R_{10}$ is hydrogen.

7. The compound of claim 6 having the following structure:

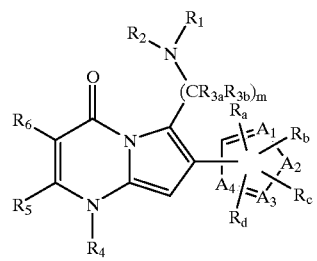

wherein
$A_1$, $A_3$ and $A_4$ are the same or different and independently nitrogen or CH;
$A_2$ is oxygen, sulfur, NH, N=N or N=CH; and
$R_a$, $R_b$, $R_c$ and $R_d$ are optional substituents that are the same or different and independently halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, hydroxy, alkoxy, aryloxy, thiol, thioalkyl, thioaryl, sulfonylalkyl, sulfonylaryl, amino, mono- or di-alkylamino, mono- or di-arylamino, —COOalkyl, —COOaryl, —CONHalkyl, —CONHaryl, —CON(alkyl)$_2$, —CON(aryl)$_2$, —NHCOalkyl, —NHCOaryl, —N(alkyl)COalkyl, —N(alkyl)COaryl, —NHSO$_2$alkyl, —NHSO$_2$aryl, N(alkyl)SO$_2$alkyl, —N(alkyl)SO$_2$aryl, —NHCONHalkyl or —NHCONHaryl;

or $R_a$ and $R_b$ taken together with the atoms to which they are attached form aryl, substituted aryl, heteroaryl or substituted heteroaryl.

8. The compound of claim 3 wherein B is $CR_{10}$ and Ar is heteroaryl.

9. The compound of claim 8 having the following structure:

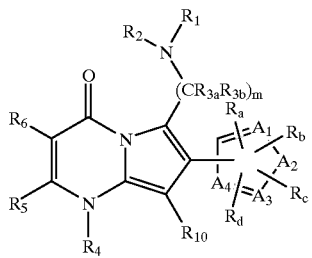

wherein
- $A_1$, $A_3$ and $A_4$ are the same or different and independently nitrogen or CH;
- $A_2$ is oxygen, sulfur, NH, N=N or N=CH; and
- $R_a$, $R_b$, $R_c$ and $R_d$ are optional substituents that are the same or different and independently halogen, nitro, cyano, alkyl, substituted alkyl, aryl, substituted aryl, arylalkyl, substituted arylalkyl, heteroaryl, substituted heteroaryl, heteroarylalkyl, substituted heteroarylalkyl, hydroxy, alkoxy, aryloxy, thiol, thioalkyl, thioaryl, sulfonylalkyl, sulfonylaryl, amino, mono- or di-alkylamino, mono- or di-arylamino, —COOalkyl, —COOaryl, —CONHalkyl, —CONHaryl, —CON(alkyl)$_2$, —CON(aryl)$_2$, —NHCOalkyl, —NHCOaryl, —N(alkyl)COalkyl, —N(alkyl)COaryl, —NHSO$_2$alkyl, —NHSO$_2$aryl, N(alkyl)SO$_2$alkyl, —N(alkyl)SO$_2$aryl, —NHCONHalkyl or —NHCONHaryl;
- or $R_a$ and $R_b$ taken together with the atoms to which they are attached form aryl, substituted aryl, heteroaryl or substituted heteroaryl.

10. The compound of claim 1 wherein $R_1$ is arylalkyl, substituted arylalkyl or heteroarylalkyl.

11. The compound of claim 10 wherein arylalkyl is benzyl and substituted arylalkyl is substituted benzyl.

12. The compound of claim 10 wherein heteroarylalkyl is —CH$_2$(heteroaryl) or —CH$_2$CH$_2$(heteroaryl).

13. The compound of claim 1 wherein $R_2$ is alkyl.

14. The compound of claim 13 wherein alkyl is methyl.

15. The compound of claim 1 wherein $R_1$ and $R_2$ taken together with the nitrogen atom to which they are attached form a heterocycle or substituted heterocycle.

16. The compound of claim 1 wherein $R_{3a}$ is hydrogen.

17. The compound of claim 1 wherein $R_{3b}$ is hydrogen.

18. The compound of claim 16 wherein $R_{3b}$ is hydrogen.

19. The compound of claim 1 where m is 1.

20. The compound of claim 1 wherein $R_4$ is arylalkyl or substituted arylalkyl.

21. The compound of claim 20 wherein arylalkyl or substituted arylalkyl is benzyl or substituted benzyl.

22. The compound of claim 1 wherein $R_5$ is hydrogen.

23. The compound of claim 1 wherein $R_6$ is —C(=O)OR$_7$.

24. The compound of claim 23 wherein $R_7$ is alkyl.

25. The compound of claim 1 wherein $R_6$ is —C(=O)NR$_7$R$_8$.

26. The compound of claim 13 wherein $R_7$ and $R_8$ are the same or different and independently alkyl or substituted alkyl.

27. The compound of claim 25 wherein $R_7$ and $R_8$ taken together with the nitrogen atom to which they are attached form a heterocycle or substituted heterocycle.

28. The compound of any one of claims 5, 7 or 9 wherein the heteroaryl moiety

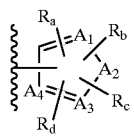

has one of the following structures:

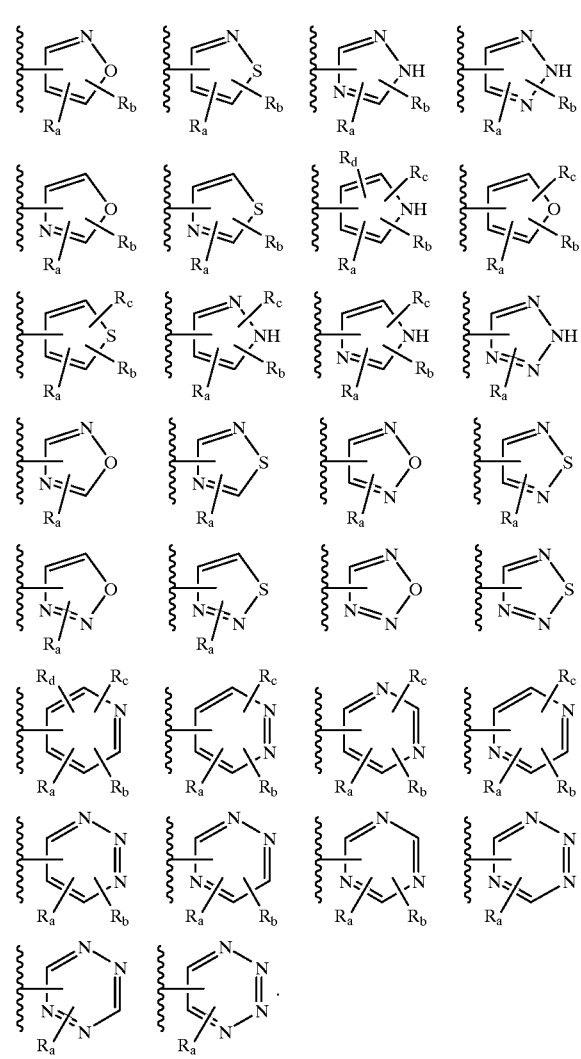

29. The compound of claim 1 wherein $R_{10}$ is halogen or cyano.

30. The compound of claim 1 wherein the compound is:

2-(2,5-Dimethylfuran-3-yl)-3-[N-methyl-(2-pyridylethyl)]aminomethyl-5-(3-pentoxycarbonyl)-7-(2-fluorobenzyl)imidazolo[1,2-a]pyrimid-4-one;

2-(1-Methylpyrrol-3-yl)-3-{N-[2-(2-pyridyl)ethyl]—N-methylaminomethyl}-5-(3-methoxyphenyl)-6-methyl-7-(2-fluorophenylmethyl)imidazolo[1,2-a]pyrimid-4-one;

2-(Thiophen-2-yl)-3-{N-[2-(2-pyridyl)ethyl]—N-methylaminomethyl}-5-(3-methoxyphenyl)-6-methyl-7-(2-fluorophenylmethyl)imidazolo[1,2-a]pyrimid-4-one;

2-(2,5-Dimethylfur-3-yl)-3-{N-[2-(2-pyridyl)ethyl]—N-methylaminomethyl}-5-(3-methoxyphenyl)-6-methyl-7-(2-fluorophenylmethyl)imidazolo[1,2-a]pyrimid-4-one;

2-(Pyrid-3-yl)-3-{N-[2-(2-pyridyl)ethyl]—N-methylaminomethyl}-5-(3-methoxyphenyl)-6-methyl-7-(2-fluorophenylmethyl)imidazolo[1,2-a]pyrimid-4-one;

1-[N-Methyl-(2-pyridylethyl)]aminomethyl-2-(4-methoxyphenyl)-3-cyano-4-(2-fluorobenzyl)-6-ethoxycarbonylpyrrolo[1,2-a]pyrimid-7-one;

1-[N-Methyl-(2-pyridylethyl)]aminomethyl-2-(2,5-dimethylfuran-3-yl)-4-(2-fluorobenzyl)-6-(3-pentoxycarbonyl)pyrrolo[1,2-a]pyrimid-7-one;

1-(N-Benzyl-N-methyl)aminomethyl-2-(4-methoxyphenyl)-3-cyano-4-(2-fluorobenzyl)-6-ethoxycarbonylpyrrolo[1,2-a]pyrimid-7-one;

1-(N-Benzyl-N-methyl)aminomethyl-2-(4-methoxyphenyl)-3-cyano-4-(2-cyanobenzyl)-6-ethoxycarbonylpyrrolo[1,2-a]pyrimid-7-one;

1-(N-Benzyl-N-methyl)aminomethyl-2-(4-methoxyphenyl)-3-cyano-4-(2-methoxybenzyl)-6-ethoxycarbonylpyrrolo[1,2-a]pyrimid-7-one;

1-(N-Benzyl-N-methyl)aminomethyl-2-(4-methoxyphenyl)-3-cyano-4-(2,4-difluorobenzyl)-6-ethoxycarbonylpyrrolo[1,2-a]pyrimid-7-one;

1-(N-Benzyl-N-methyl)aminomethyl-2-(4-isobutoxyphenyl)-3-cyano-4-(2-fluorobenzyl)-6-ethoxycarbonylpyrrolo[1,2-a]pyrimid-7-one;

1-[N-Methyl-(2-pyridylethyl)]aminomethyl-2-(2,5-dimethylfuran-3-yl)-4-(2-fluorobenzyl)-6-(3-pentoxycarbonyl)pyrrolo[1,2-a]pyrimid-7-one;

1-[N-Methyl-(2-pyridylethyl)]aminomethyl-2-(2,5-dimethylfuran-3-yl)-4-(2-fluorobenzyl)-6-(3-pentoxycarbonyl)imidazolo[1,2-a]pyrimid-7-one;

1-(N-Benzyl-N-methyl)aminomethyl-2-(4-isobutoxyphenyl)-3-fluoro-4-(2-fluorobenzyl)-6-ethoxycarbonylpyrrolo[1,2-a]pyrimid-7-one; or 1-[N-Methyl-(2-pyridylethyl)]aminomethyl-2-(4-isobutoxyphenyl)-3-fluoro-4-(2-fluorobenzyl)-6-ethoxycarbonylpyrrolo[1,2-a]pyrimid-7-one.

31. A pharmaceutical composition comprising a compound of claim 1 and a pharmaceutically acceptable carrier.

32. A method for antagonizing gonadotropin-releasing hormone in a subject in need thereof, comprising administering to the subject an effective amount of the compound of claim 1.

33. A method for treating a sex-hormone related condition of a subject in need thereof, comprising administering to the subject an effective amount of the pharmaceutical composition of claim 31.

34. The method of claim 33 wherein the sex-hormone related condition is cancer, benign prostatic hypertropy or myoma of the uterus.

35. The method of claim 34 wherein the cancer is prostatic cancer, uterine cancer, breast cancer or pituitary gonadotroph adenomas.

36. The method of claim 33 wherein the sex-hormone related condition is endometriosis, polycystic ovarian disease, uterine fibroids or precocious puberty.

37. A method for preventing pregnancy of a subject in need thereof, comprising administering to the subject an effective amount of the pharmaceutical composition of claim 31.

38. A method for treating lupus erythematosis, irritable bowel syndrome, premenstrual syndrome, hirsutism, short stature or sleep disorders in a subject in need thereof, comprising administering to the subject an effective amount of the pharmaceutical composition of claim 31.

* * * * *